(12) United States Patent
Needham et al.

(10) Patent No.: US 11,224,624 B2
(45) Date of Patent: Jan. 18, 2022

(54) MODULATION OF MICROBIAL SYNTHESIS OF 4-ETYLPHENOL AND 4-ETHYLPHENYL SULFATE IN BEHAVIOR AND DISEASE

(71) Applicants: California Institute of Technology, Pasadena, CA (US); The Regents of the University of California, Oakland, CA (US)

(72) Inventors: Brittany D. Needham, Pasadena, CA (US); Sarkis K. Mazmanian, Pasadena, CA (US); Gil Sharon, Pasadena, CA (US); Masanori Funabashi, San Francisco, CA (US); Michael A. Fischbach, San Francisco, CA (US); Elaine Y. Hsiao, Pasadena, CA (US); Paul H. Patterson, Pasadena, CA (US)

(73) Assignees: CALIFORNIA INSTITUTE OF TECHNOLOGY, Pasadena, CA (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 119 days.

(21) Appl. No.: 16/485,403

(22) PCT Filed: Feb. 13, 2018

(86) PCT No.: PCT/US2018/018069
§ 371 (c)(1),
(2) Date: Aug. 12, 2019

(87) PCT Pub. No.: WO2018/152133
PCT Pub. Date: Aug. 23, 2018

(65) Prior Publication Data
US 2019/0374588 A1 Dec. 12, 2019

Related U.S. Application Data

(60) Provisional application No. 62/458,716, filed on Feb. 14, 2017.

(51) Int. Cl.
*A61K 35/741* (2015.01)
*A61K 35/747* (2015.01)
(Continued)

(52) U.S. Cl.
CPC .......... *A61K 35/747* (2013.01); *A23L 33/135* (2016.08); *A61K 9/0031* (2013.01); *A61K 9/0053* (2013.01); *A61P 25/22* (2018.01)

(58) Field of Classification Search
CPC ................................................... A61K 35/741
See application file for complete search history.

(56) References Cited

U.S. PATENT DOCUMENTS

| | | |
|---|---|---|
| 2013/0195802 A1 | 8/2013 | Moore |
| 2014/0065132 A1 | 3/2014 | Hsiao et al. |
| 2017/0173086 A1* | 6/2017 | Boyle .................. A61K 35/741 |

FOREIGN PATENT DOCUMENTS

| | | |
|---|---|---|
| CN | 104546932 | 4/2015 |

OTHER PUBLICATIONS

Christensen et al., 2016, Prevalence and Characteristics of Autism Spectrum Disorder Among Children Aged 8 Years—Autism and Developmental Disabilities Monitoring Network, 11 Sites, United States, 2012. MMWR Surveill. Summ. 65, 1-23.
(Continued)

*Primary Examiner* — Rosanne Kosson
(74) *Attorney, Agent, or Firm* — Knobbe, Martens, Olson & Bear LLP

(57) ABSTRACT

Some embodiments relate to genetically engineered bacterial strains for modulation of levels of the bacterial metabolite 4-ethylphenol (4EP) and its sulfated form, 4-ethylphenyl sulfate (4EPS). In some embodiments, the bacteria reduce or inhibit production of 4EP or 4EPS in the gut of a subject. The bacteria can ameliorate, delay the onset or reduce the likelihood of one or more symptoms associated with anxiety and/or autism spectrum disorder (ASD) in the subject.

20 Claims, 21 Drawing Sheets
Specification includes a Sequence Listing.

Detectable 4EPS in plasma

(51) Int. Cl.
*A23L 33/135* (2016.01)
*A61P 25/22* (2006.01)
*A61K 9/00* (2006.01)

(56) References Cited

OTHER PUBLICATIONS

Diagnostic and Statistical Manual of Mental Disorders, Fourth Edition (DSM-IV-TR), American Psychiatric Association, 2000.
Fombonne, 2009, Epidemiology of pervasive developmental disorders, Pediatr. Res. 65, 591-598.
Green and Sambrook, Molecular Cloning: A Laboratory Manual. Cold Spring Harbor Laboratory Press, N.Y., (4th Edition) (2012).
King et al., 2009, Diagnostic change and the increased prevalence of autism. Int. J. Epidemiol. 38, 1224-1234.
Koropatkin et al., Jul. 2008, Starch catabolism by a prominent human gut symbiont is directed by the recognition of amylose helices, Structure, 16(7):1105-1115.
Sandin et al., 2017, The Heritability of Autism Spectrum Disorder. JAMA 318, 1182-1184.
International Search Report and Written Opinion dated Jul. 19, 2018 in PCT/US18/18069.

* cited by examiner

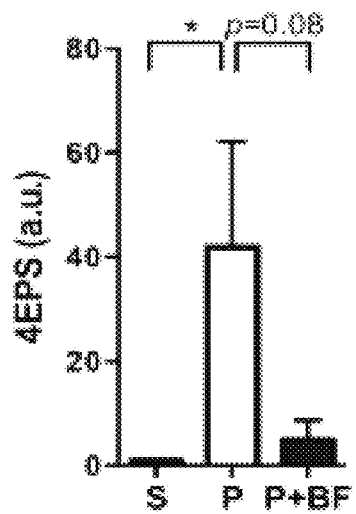
FIG 1A
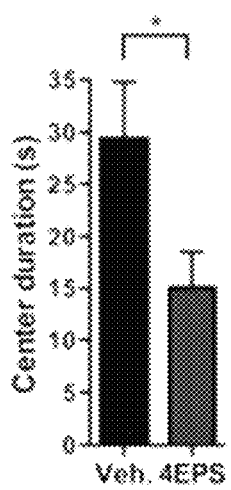 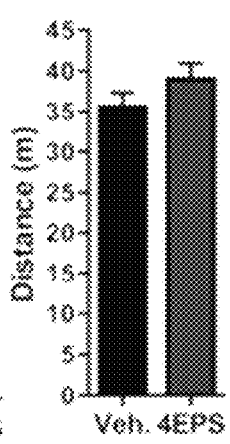 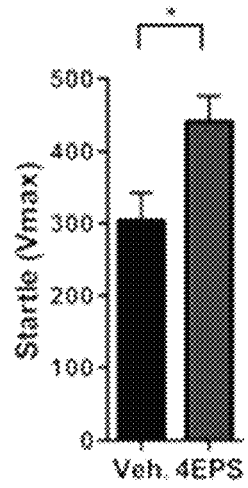 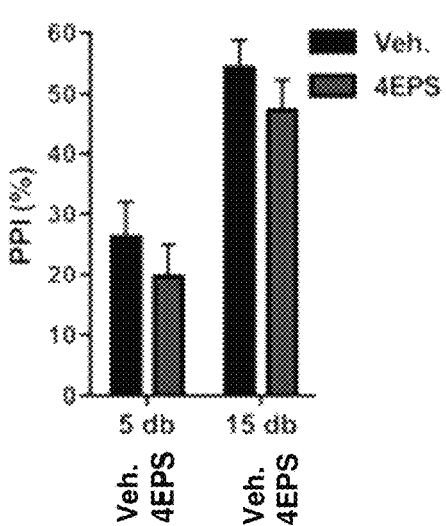
FIG 1B　　FIG 1C　　FIG 1D　　FIG 1E

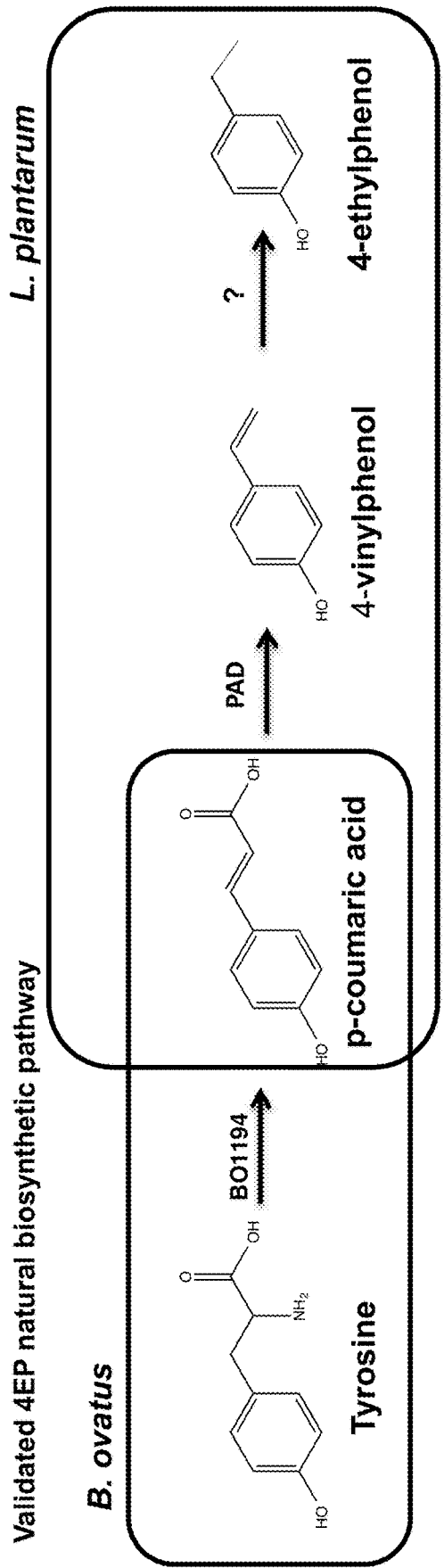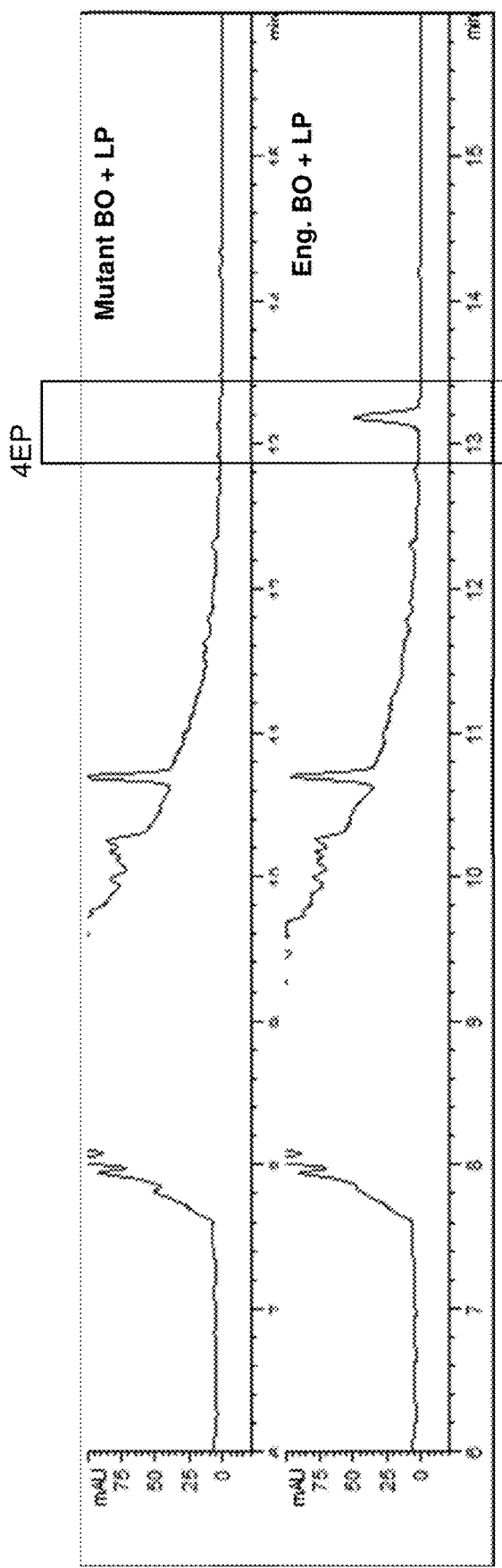
FIG. 3A
FIG. 3B

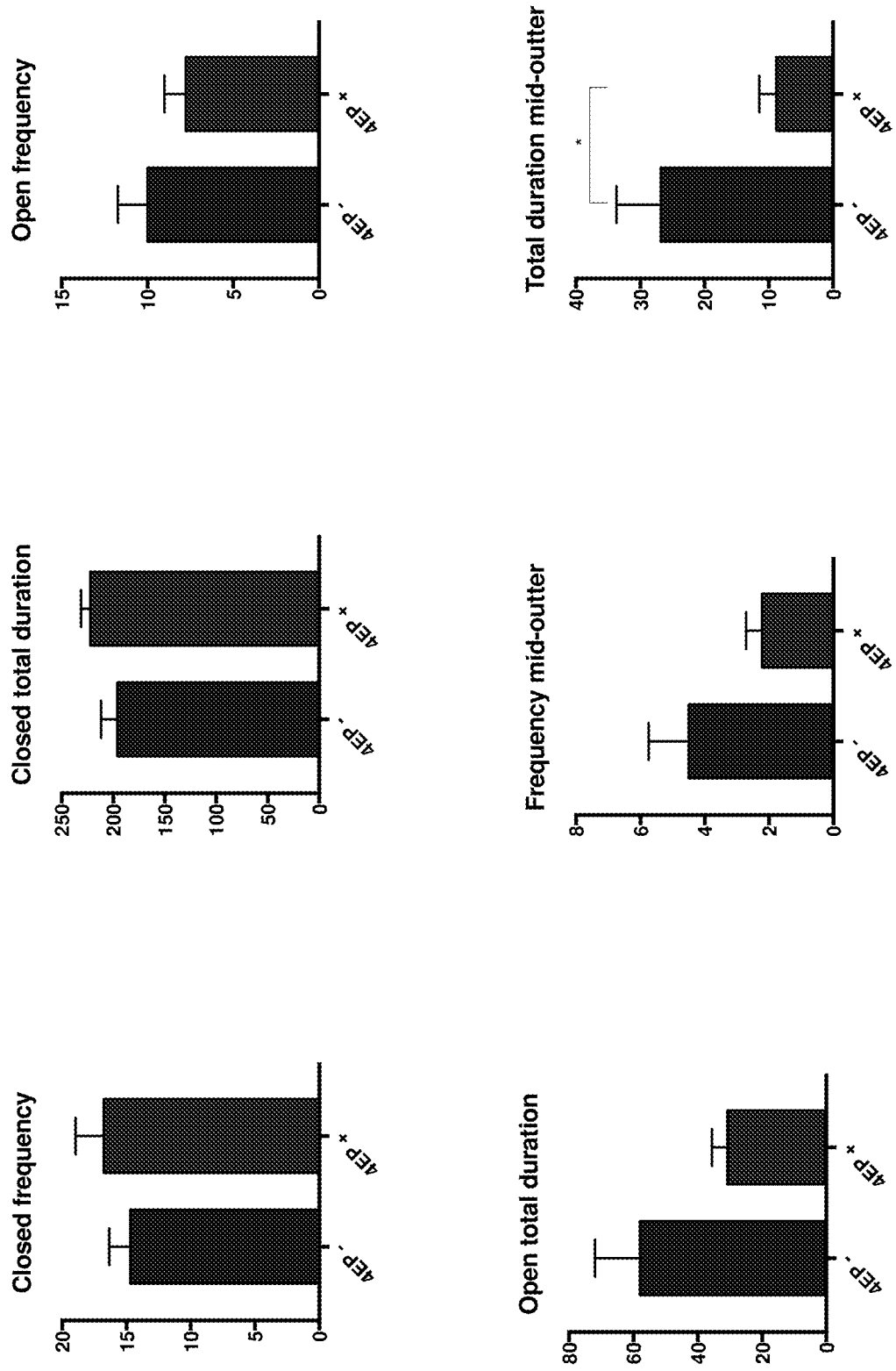
FIG. 6A (part I)

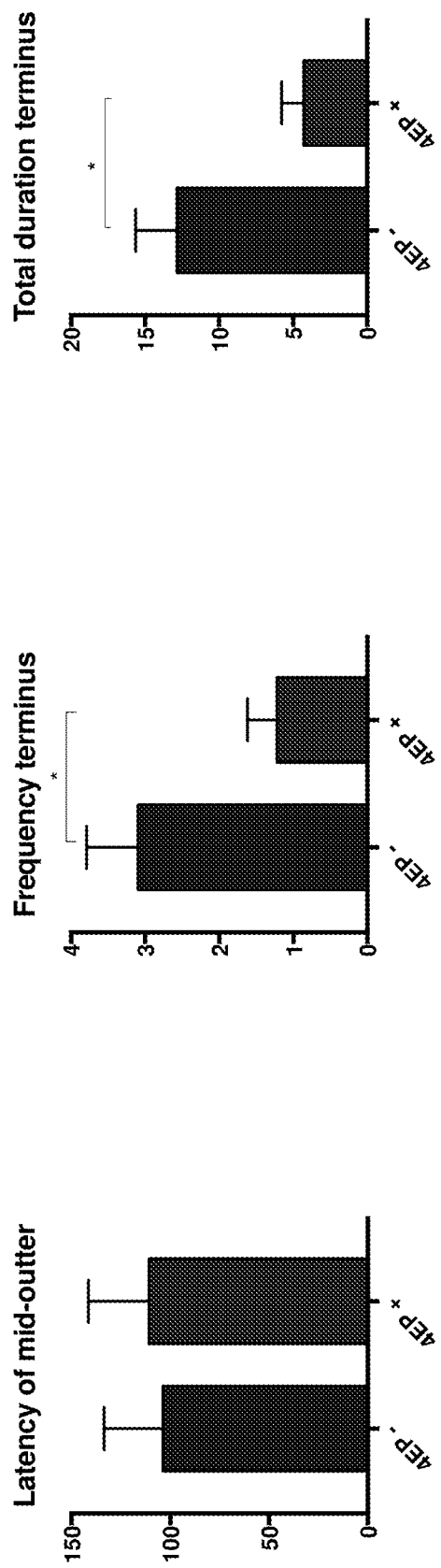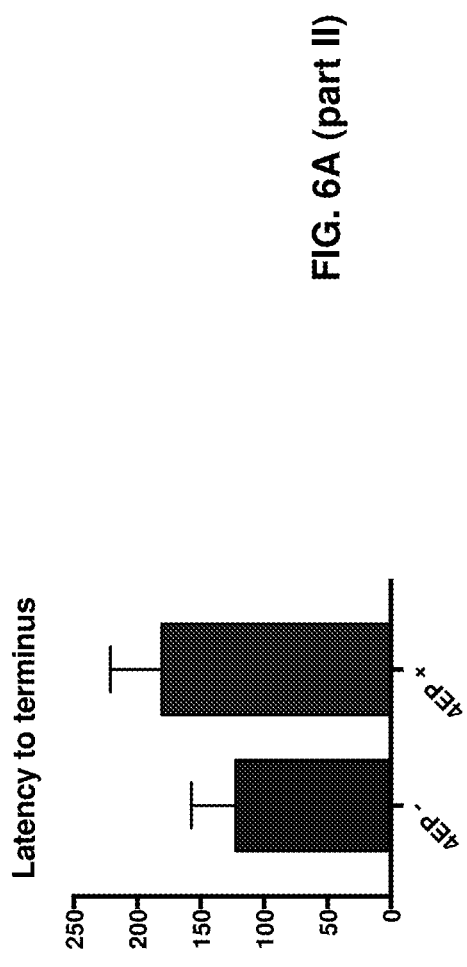
FIG. 6A (part II)

>BACOVA_01194.dna   (1524 bp)

ATGATAGCTGACAAAAGTATAAATTTAGATACCCTTCATAAAGTATTGTTTGATAATGAGAAGCTGAAAC
TCTCTGAAGAATGTATTCGAAAAGTAGAAGAAAGCTTCGATTTTCTGCAATCCTTTTCCAGCGATAAGAT
TATTTATGGTATCAATACGGGGTTCGGCCCAATGGCACAATACAGAATAGAAGATCAGTCATTGATCGAC
CTTCAGTATAATATCATCCGAAGCCATTCCACCGGTGCCGGCAAACCGCTTCCCGAACTTTATGTAAAAG
CAGCTATGATTGCCCGTTTGTACACTTTCTACAAGGGAAGTCAGGAGTGCATCTGGAACTGGTTTCTCT
CCTCTGTGAATTTATCAACCGCGGAATTTATCCGTTCATACCCGAACACGGAAGTGTAGGTGCCAGCGGC
GATCTCGTACAACTGGCCCATATCGCCCTGACGTTAATAGGGGAAGGGGAAGTTTTTATCAGGGTAAAT
TGTGTAACGCAGCTACGGTACTTCAGGAAAACGGCCTGAAACCTTTTCCATGCGTATTCGTGAAGGTTT
ATCCGTTACAAACGGTACTTCTGTAATGACAGGCATCGGTATTGTCAATCTGATTTATGCAAAAAACTA
CTCCGTTGGTCGGTGGCTGCCTCTGTAATGATGAATGAGATTGCCGCCTCTTATGATGATTTATGGCAC
AGGCATTAAACGAGGCCAAGCATCATAAAGGTCAACAAGAGATAGCTGCTATGATGAGAGAATGGGTGGC
AGGCAGTAAATCCGTGCTTCAAAGAGAGAACGAGCTATACAACCAGGTGCATAAAGAGAAAATCTTCGAA
CACAAAGTACAGCCCTATTATTCCTTGCGATGTGTTCCGCAAATACTCGGTCCTATTTACGATGAACTGG
AGAATGCGGAAGAAGTATTAATAAACGAAATAAATTCCGCCTGTGACAATCCGATTGTCGATCCGGATAC
ACAAAATATTTATCATGGCGGCAACTTCCACGGAGATTACATTTCTTTCGAAATGGACAAGTTGAAAATT
GCTGTGACCAAGCTGACTATGCTTTGCGAAAGACAAATTAACTATCTGTTCCACGACCGTATCAATGGCA
TCCTGCCTCCGTTTGTAAATTTGGGAGTGCTTGGATTGAACTATGGTTTACAGGCTTCGCAATTCACTGC
AACCTCCACCACAGCGGAGTGTCAGACATTATCAAATCCGATGTATGTACACAGTATCCCCAACAACAAT
GATAATCAGGATATTGTCAGCATGGGAACCAACTCGGCTCTATTAGCAAAACAGTCATTGAGAATTCTT
ATCAGGTGATGGCTATCCAGTTTATGGGAATGGCACAAGCTATCGACTACCTGAAAATACAGGATCGCCT
AAGTTCCAAAAGCAGGCAGGTTTATGAAGAAATACGCAGTTTCTTCCCTGTATTTACCAATGACACACCT
AAATATAAAGAGATAGAAATGATGATAGACTATCTCAAAAAAGAAGATAAATAA (SEQ ID NO: 1)

FIG. 12A

>NC_004567.2:3286815-3287351 Lactobacillus plantarum WCFS1, complete
genome
ATGACAAAAACTTTTAAAACACTTGATGACTTTCTCGGCACACACTTTATCTACACTTATGATAACGGCT
GGGAATACGAGTGGTACGCCAAGAACGACCACACCGTTGATTACCGAATCCACGGTGGGATGGTTGCCGG
TCGTTGGGTCACTGATCAAAAGCTGACATCGTCATGTTGACCGAAGGCATTTACAAAATTTCTTGGACT
GAACCAACTGGGACTGACGTTGCACTAGACTTCATGCCCAATGAGAAGAAACTACACGGTACGATTTCT
TCCCAAAGTGGGTTGAAGAACACCCTGAAATTACGGTCACTTACCAAAACGAACACATCGATTTAATGGA
ACAGTCTCGTGAAAGTATGCCACTTATCCAAAACTAGTTGTACCCGAATTTGCCAATATTACTTACATG
GGCGACGCCGGCCAAAACAACGAAGATGTAATCAGTGAAGCACCTTACAAAGAAATGCCGAATGATATTC
GCAACGGCAAGTACTTTGATCAAAACTACCATCGTTTAAATAAGTAA   (SEQ ID NO:2)

FIG. 12B

```
>bcPAD.dna   (522 bp)

ATGAAGTACAGTAAAAGACTAAGGAGAGTGTGTAAGATGGAAAACTTTATCGGAAGCCACATGATTTATA
CGTATGAAAACGGATGGGAATACGAGATTTATATTAAAAACGACCATACAATTGATTATAGAATTCATAG
CGGAATGGTTGCCGGACGCTGGGTTCGAGATCAGGAAGTGAATATTGTCAAACTGACAGAAGGCGTATAT
AAAGTGTCTTGGACAGAGCCGACTGGCACGGATGTTTCATTAAACTTTATGCCAAATGAAAAACGCATGC
ATGGCATTATTTTCTTCCCGAAATGGGTGCATGAACATCCTGAAATTACGGTTTGCTACCAAAATGACCA
CATTGATTTGATGAAAGAATCCCGCGAAAAATATGAAACGTATCCAAAATACGTTGTACCTGAATTTGCG
GAAATTACATTTCTGAAAAATGAAGGAGTCGACAACGAAGAAGTGATTTCGAAGGCTCCTTATGAGGGAA
TGACAGACGATATTCGCGCGGGAAGATTATAA
```
(SEQ ID NO:5)

FIG. 12C

MODULATION OF MICROBIAL SYNTHESIS OF 4-ETYLPHENOL AND 4-ETHYLPHENYL SULFATE IN BEHAVIOR AND DISEASE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. The present Application is the U.S. national phase of International Application No. PCT/US2018/018069, filed Feb. 13, 2018, which claims the benefit of U.S. Provisional App. No. 62/458,716, filed Feb. 14, 2017, which is hereby incorporated by reference in its entirety.

STATEMENT REGARDING FEDERALLY SPONSORED R&D

This invention was made with government support under Grant No. MH100556, GM099535 and DK113598 awarded by the National Institutes of Health. The government has certain rights in the invention.

REFERENCE TO SEQUENCE LISTING

This application is filed with an electronic sequence listing entitled CALTE129WOSEQLIST.txt, created on Feb. 13, 2018 which is 20,899 bytes in size, and updated by a filed entitled CALTE129NPSEQUENCE.TXT, created on Aug. 13, 2019, which is 21,054 bytes in size. The information in the electronic sequence listing is hereby incorporated by reference in its entirety.

BACKGROUND

A number of behavior disorders are known. Anxiety disorders are a class of disorders that can involve various degrees of worry, fear, and distress that can interfere with normal function. Examples of disorders associated with anxiety include depression, chronic illness, eating disorders, headaches, hoarding disorder, irritable bowel syndrome, sleep disorders, substance use disorders, attention deficit/hyperactive disorders, chronic pain, and fibromyalgia. Autism spectrum disorders (ASD) are a group of neurodevelopmental conditions with a broad range of manifestations involving altered social communication and interaction, as well as repetitive, stereotyped behaviors. The prevalence of ASD in the US, as of 2012, is 14.6 per 1,000 children (Christensen et al., 2016), with 1 million cases currently and evidence that diagnoses are rising (Fombonne, 2009; King and Bearman, 2009). ASD heritability has been estimated as high as 83%, and the non-shared environmental influence at 17% (Sandin et al., 2017).

Metabolites produced by gut bacteria have significant effects on host health. In various disease states, the levels and localization of these bacterial-derived molecules can fluctuate. Described herein are experiments demonstrating direct effects of the bacterial metabolite 4-ethylphenol (4EP) and its sulfated form, 4-ethylphenyl sulfate (4EPS) on symptoms of behavioral disorders such as ASD and anxiety, and embodiments related to compositions, methods, and uses for improving behavioral performance, for example in anxiety and/or ASD.

FIELD

Some embodiments herein relate to genetically engineered bacterial strains for modulation of levels of the bacterial metabolite 4-ethylphenol (4EP) and its sulfated form, 4-ethylphenyl sulfate (4EPS). In some embodiments, the bacteria reduce or inhibit production of 4EP or 4EPS in the gut of a subject, and ameliorate, delay the onset of or reduce the likelihood of one or more symptoms associated with anxiety and/or ASD in the subject.

SUMMARY

Some embodiments include a composition or product combination comprising a genetically engineered *Bacteroides ovatus* comprising a loss-of-function mutation in a gene encoding BO1194, and/or a genetically engineered *Lactobacillus plantarum* comprising a loss-of function mutation in a gene encoding phenolic acid decarboxylase (PAD). In some embodiments, the composition or product combination according to any of the foregoing or following is formulated for oral or rectal administration to a mammalian subject. In some embodiments, the composition or product combination according to any of the foregoing or following is selected from the group consisting of: a probiotic composition or product combination, a pharmaceutical composition or product combination, a dietary supplement, and a food; or a combination of two or more of the listed items. In some embodiments, the composition or product combination according to any of the foregoing or following further comprises a polyphenol. In some embodiments, the polyphenol comprises quercetin and/or curcumin. In some embodiments, the composition or product combination according to any of the foregoing or following comprises the genetically engineered *Bacteroides ovatus*. In some embodiments, for the composition or product combination according to any of the foregoing or following, the loss-of-function mutation in the gene encoding BO1194 comprises a deletion, insertion, substitution, rearrangement, or frameshift. In some embodiments, the composition or product combination according to any of the foregoing or following comprises the genetically engineered *Lactobacillus plantarum*. In some embodiments, for the composition or product combination according to any of the foregoing or following, the loss-of-function mutation in the gene encoding PAD comprises a deletion, insertion, substitution, rearrangement, or frameshift. In some embodiments, the composition or product combination according to any of the foregoing or following comprises the genetically engineered *Bacteroides ovatus* and the genetically engineered *Lactobacillus plantarum* together in a single composition. In some embodiments, the composition or product combination according to any of the foregoing or following comprises the genetically engineered *Bacteroides ovatus* and the genetically engineered *Lactobacillus plantarum* is separate compositions. In some embodiments, for the composition or product combination according to any of the foregoing or following, the genetically engineered *Bacteroides ovatus* is deficient in the production of p-coumaric acid. In some embodiments, for the composition or product combination according to any of the foregoing or following, the genetically engineered *Lactobacillus plantarum* is deficient in the production of 4-vinylphenol. In some embodiments, the composition or product combination according to any of the foregoing or following comprises the genetically engineered *Bacteroides ovatus* comprising the loss-of-function mutation in the gene encoding BO1194, and comprises no more than $10^6$ cfu of *Lactobacillus plantarum*. In some embodiments, the composition or product combination according to any of the foregoing or following comprises the genetically engineered *Lactobacillus plantarum* comprising the loss-of-function mutation in the gene encoding PAD, and comprises no more than $10^6$ cfu of *Bacteroides ovatus*, for example no more than $10^6$, $10^5$, $10^4$, or $10^3$ cfu. In some embodiments, the composition or product combination according to any of the foregoing or following comprises at least $10^4$ cfu of the genetically engineered *Bacteroides ovatus*, for example, at least $10^4$ cfu, $10^5$ cfu, or $10^6$ cfu. In some embodiments, the composition or product combination according to any of the foregoing or following comprises at least $10^4$ cfu of the genetically engineered *Lactobacillus plantarum*, for example, at least $10^4$ cfu, $10^5$ cfu, or $10^6$ cfu. In some embodiments, the composition or product combination according to any of the foregoing or following comprises at least $10^4$ cfu of the genetically engineered *Bacteroides ovatus* and at least $10^4$ cfu of the genetically engineered *Lactobacillus plantarum*, for example, at least $10^4$ cfu, $10^5$ cfu, and/or $10^6$ cfu of each. In some embodiments, the composition or product combination according to any of the foregoing or following further comprises *Bacteroides fragilis* and/or *Bacteroides thetaiotaomicro*. In some embodiments, the composition or product combination according to any of the foregoing or following is for use in ameliorating, delaying the onset of, or decreasing the likelihood of a symptom associated with anxiety and/or autism spectrum disorder (ASD) in a subject. In some embodiments, for the composition or product combination for use according to any of the foregoing or following, the use comprises inhibiting production of 4-ethylphenol (4EP) and/or 4-ethylphenyl sulfate (4EPS) in the subject, thus ameliorating, delaying the onset of, or decreasing the likelihood of the symptom associated with anxiety and/or ASD. In some embodiments, for the composition or product combination according to any of the foregoing or following, the use comprises ameliorating, delaying the onset of, or decreasing the likelihood of the symptom associated with anxiety. In some embodiments, for the composition or product combination according to any of the foregoing or following, the use comprises ameliorating, delaying the onset of, or decreasing the likelihood of the symptom associated with ASD. In some embodiments, for the composition or product combination according to any of the foregoing or following, the subject is selected as being within a class of subjects that should receive the composition. In some embodiments, for the composition or product combination according to any of the foregoing or following, the subject is determined to have anxiety, or a level of 4EPS in a sample of the subject is higher than that of a non-anxiety or non-ASD control subject, thus selecting the subject as being within the class of subjects that should receive the composition.

Some embodiments include a composition comprising quercetin and/or curcumin for use in ameliorating, delaying the onset of, or decreasing the likelihood of a symptom associated with anxiety and/or ASD in a subject. In some embodiments, the use according to any of the foregoing or following comprises inhibiting production of 4-ethylphenyl sulfate (4EPS) in the subject, thus ameliorating delaying the onset of, or decreasing the likelihood of a symptom associated with anxiety. In some embodiments, for the composition for use according to any of the foregoing or following (and comprising quercetin and/or curcumin), the subject is selected as being within a class of subjects that should receive the composition. In some embodiments, for the composition for use according to any of the foregoing or following (and comprising quercetin and/or curcumin), (i) the subject is determined to have a symptom associated with anxiety, or (ii) a level of 4EPS in a sample of the subject is higher than that of a non-anxiety control subject, thus selecting the subject as being within a class of subjects that should receive the composition.

Some embodiments include a method of reducing or inhibiting production of 4-ethylphenol (4EP) and/or 4-ethylphenyl sulfate (4EPS) in a subject in need thereof. The method can comprise administering to the subject a composition or product combination comprising a genetically engineered *Bacteroides ovatus* comprising a loss-of-function mutation in a gene encoding BO1194, and/or a genetically engineered *Lactobacillus plantarum* comprising a loss-of-function mutation in a gene encoding phenolic acid decarboxylase (PAD) (for example, a product or composition as described herein). The method can include permitting the genetically engineered *Bacteroides ovatus* and/or the genetically engineered *Lactobacillus plantarum* to proliferate in a gastrointestinal tract of the subject. Thus, production of 4EP and/or 4EPS in the subject is reduced or inhibited. In some embodiments, for the method according to any of the foregoing or following, reducing the levels of 4EP and/or 4EPS ameliorates, delays the onset of, or decreases the likelihood of a symptom associated with anxiety and/or ASD in the subject. In some embodiments, the method according to any of the foregoing or following further comprises, prior to said administering, selecting the subject as being within a class of subjects that are in need of receiving the composition or product combination. In some embodiments, for the method according to any of the foregoing or following, the selecting comprises identifying the subject as having a symptom associated with anxiety and/or ASD. In some embodiments, for the method according to any of the foregoing or following, the selecting comprises detecting a level of 4EP and/or a level of 4EPS in a sample derived from the subject. In some embodiments, the method according to any of the foregoing or following further comprises administering a polyphenol to the subject. By way of example, the polyphenol can comprise quercetin and/or curcumin. In some embodiments, for the method according to any of the foregoing or following, the composition or product combination comprises the genetically engineered *Bacteroides ovatus*. In some embodiments, for the method according to any of the foregoing or following, the loss-of-function mutation in the gene encoding BO1194 comprises a deletion, insertion, substitution, rearrangement, or frameshift. In some embodiments, for the method according to any of the foregoing or following, the composition or product combination comprises at least $10^4$ cfu of the genetically engineered *Bacteroides ovatus* for example, at least $10^4$ cfu, $10^5$ cfu, or $10^6$ cfu. In some embodiments, for the method according to any of the foregoing or following, the composition or product combination comprises no more than $10^6$ cfu of *Lactobacillus plantarum*, for example no more than $10^6$, $10^5$, $10^4$, or $10^3$ cfu. In some embodiments, for the method according to any of the foregoing or following, the composition or product combination comprises the genetically engineered *Lactobacillus plantarum*. In some embodiments, for the method according to any of the foregoing or following, the loss-of-function mutation in the gene encoding PAD comprises a deletion, insertion, substitution, rearrangement, or frameshift. In some embodiments, for the method according to any of the foregoing or following, the composition or product combination comprises at least $10^4$ cfu of the genetically engineered *Lactobacillus plantarum* for example, at least $10^4$ cfu, $10^5$ cfu, or $10^6$ cfu. In some embodiments, for the method according to any of the foregoing or following, the composition or product combination comprises no more than $10^6$ cfu of *Bacteroides ovatus*, for example no more than $10^6$, $10^5$, $10^4$, or $10^3$ cfu.

In some embodiments, for the method according to any of the foregoing or following, the composition or product combination comprises the genetically engineered *Bacteroides ovatus* and the genetically engineered *Lactobacillus plantarum*. In some embodiments, for the method according to any of the foregoing or following, the genetically engineered *Bacteroides ovatus* and the genetically engineered *Lactobacillus plantarum* are administered in a single composition. In some embodiments, for the method according to any of the foregoing or following, the genetically engineered *Bacteroides ovatus* and the genetically engineered *Lactobacillus plantarum* are administered in separate compositions. In some embodiments, for the method according to any of the foregoing or following, the genetically engineered *Bacteroides ovatus* and the genetically engineered *Lactobacillus plantarum* are administered at separate times. In some embodiments, for the method according to any of the foregoing or following, the genetically engineered *Bacteroides ovatus* and the genetically engineered *Lactobacillus plantarum* are administered at the same time. In some embodiments, for the method according to any of the foregoing or following, the genetically engineered *Bacteroides ovatus* and the genetically engineered *Lactobacillus plantarum* are administered at separate times, or at the same time. In some embodiments, for the method according to any of the foregoing or following, the subject is germ free. In some embodiments, for the method according to any of the foregoing or following, the method further comprises administering an antibiotic to the subject prior to administering the composition or product combination. The antibiotic can reduce a total quantity of gut bacteria of the subject by at least 80% prior to the administering of the composition, for example reducing the quantity of gut bacteria of the subject by at least 80%, 85%, 90%, 95%, 97%, 98%, 99%, or 99.9%.

Some embodiments include a method of reducing or inhibiting production of 4-ethylphenol (4EP) and/or 4-ethylphenyl sulfate (4EPS) in a subject in need thereof, the method comprising administering an amount of polyphenol to the subject. In some embodiments, the polyphenol comprises quercetin and/or curcumin. In some embodiments, the amount is effective to reduce and/or inhibit sulfation of the 4EP and/or 4EPS. In some embodiments, reducing the levels of 4EP and/or 4EPS ameliorates, delays the onset of, or decreases the likelihood of a symptom associated with anxiety in the subject. In some embodiments, the method further comprises, prior to the administering, selecting the subject as being within a class of subjects that are in need of receiving the composition. In some embodiments, the selecting comprises identifying the subject as having a symptom associated with anxiety. In some embodiments, the selecting comprises detecting a level of 4EP and/or a level of 4EPS in a sample derived from the subject. In some embodiments, for any method of reducing or inhibiting production of 4EP and/or 4EPS as described herein, the method, further comprising administering to the subject a composition or product combination comprising a genetically engineered *Bacteroides ovatus* comprising a loss-of-function mutation in a gene encoding BO1194, and/or a genetically engineered *Lactobacillus plantarum* comprising a loss-of-function mutation in a gene encoding phenolic acid decarboxylase (PAD) (for example, a composition or product composition as described herein).

BRIEF DESCRIPTION OF THE DRAWINGS

FIGS. 1A-E are a series of graphs showing quantification and effects of 4EPS on mice in accordance with some embodiments herein. FIG. 1A shows relative quantification of 4EPS detected by GC/LC-MS. Wildtype mice were injected i.p. with saline or 30 mg/kg 4EPS potassium salt daily from 3 to 6 weeks of age. FIG. 1B shows center durations. FIG. 1C shows distance from center. FIG. 1D shows startle (Vmax). FIG. 1E shows prepulse inhibition (PPI)(%).

FIGS. 2A and 2C each show a 4EPS standard curve. FIG. 2B shows % detectable 4EPS in plasma samples. FIG. 2D shows % samples above lowest standard for 4EPS in plasma. "Gp" refers to general population, and "Au" refers to an ASD population.

FIGS. 3A-C are a series of schematics and graphs showing 4EP and 4EPS synthesis of some embodiments. FIG. 3A shows the validated 4EP natural biosynthetic pathway. FIG. 3B shows in vitro 4EP production. FIG. 3C shows 4EPS levels in urine for engineered bacterial pairs.

FIG. 4A show a schematic of movements in an elevated plus maze, and FIGS. 4B-C are graphs showing responses in the elevated plus maze. FIG. 4D shows a schematic of movements in a light/dark box, and FIGS. 4E-F show responses in the light/dark box. FIG. 4G is a schematic of movements in an open field arena, and FIGS. 4H-I are graphs showing responses in the open field arena.

FIG. 5A shows frequency of entries in to a segment of the arena as well as total duration of time spent there. FIG. 5B shows total distance moved and total time spent moving.

FIGS. 6A-B are a series of graphs showing elevated plus maze (EPM) behavior of mice colonized with 4EP+/− bacterial pairs of some embodiments herein. FIG. 6A is a series of graphs showing frequency of entries in to a segment of the maze as well as total duration of time spent there. FIG. 6B is a graph showing total distance moved.

FIG. 11A is a graph illustrating the detection of sulfation of 4EP and PC. FIG. 11B is a graph illustrating LCMS detection of sulfated donor. FIG. 11C is a graph illustrating that Quercetin inhibits SULT1A1 in vitro. FIG. 11D is a graph illustrating that SULT1A1 (sulfotransferase family 1A member 1) is expressed in GI tract of colonized mice. FIG. 11E is a graph illustrating tissue sulfation of 4EP.

FIG. 12A is a schematic diagram illustrating a *B. ovatus* 01194 coding sequence (SEQ ID NO: 1) of some embodiments herein. FIG. 12B is a schematic diagram illustrating a *Lactobacillus plantarum* phenolic acid decarboxylase (PAD) coding sequence (SEQ ID NO: 2) of some embodiments herein. FIG. 12C is a schematic diagram illustrating a *Bacillus subtilis* phenolic acid decarboxylase (PAD) coding sequence (SEQ ID NO: 5) of some embodiments herein.

DETAILED DESCRIPTION

Figure 2A:
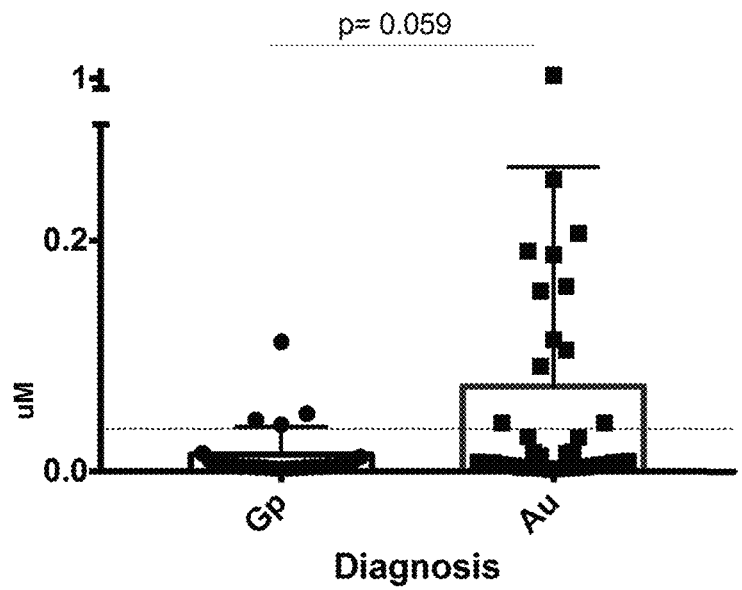
FIGS. 2A-D are a series of graphs showing 4EPS detection in human ASD in accordance with some embodiments herein.

Decreasing or inhibiting the production of 4EPS (or one or more of its precursors, such as 4EP, 4-vinylphenol, and/or p-coumaric acid) in accordance with some embodiments herein can ameliorate, delay the onset of, or lower the liklihoood of symptoms of anxiety and/or autism spectrum disorder (ASD) in a mammal in need thereof. It is reported herein that the metabolite 4EPS is elevated in the serum of subjects that suffer from symptoms associated with anxiety and/or autism spectrum disorder (ASD) (it is also noted that symptoms of ASD can sometimes include anxiety and its associated symptoms), including the maternal immune activation (MIA) mouse model of anxiety disorder and autism spectrum disorder (Example 1, FIG. 1A), and in human ASD patients (Example 2, FIGS. 2A-D). Furthermore, administering 4EPS to wild-type mice induced anxiety behaviors in these mice (Examples 1, 4, FIGS. 1B-D, 4D-I). 4EPS is produced by bacteria such as bacteria in the gut, and the 4EPS synthesis pathway has been characterized herein. Notably, the synthesis of 4EP (which is sulfated to become 4EPS) is not produced in any one bacteria, but rather involves two bacteria that each perform a portion of the synthesis, *Bacteroides ovatus*, and *Lactobacillus plantarum*. (Example 3, FIG. 3A). Mutant *B. ovatus* comprising a deletion of the gene encoding BO1194 were constructed, were deficient in 4EPS production, and further, inhibited production of 4EPS when used to colonize mice (Example 3, FIGS. 3B, 3C). Moreover, overexpression of native BO1194 and *Bacillus subtilis* phenolic acid decarboxylase (PAD) in *B. ovatus* contributed to the production of 4EP (Example 3, FIG. 3B). Colonization of mice with the bacteria comprising the deletion of the gene encoding BO1194 improved measurements of anxiety, for example, increasing frequency in center and total duration in center, and decreasing total duration at the wall and mean duration at the wall in an open field arena (Example 5, FIG. 5A). Furthermore, the colonization increased total duration in center and total duration in center, and decreased total duration at wall and mean duration at wall in an elevated plus maze (Example 6, FIG. 6A). Furthermore, the colonization ameliorated symptoms associated with ASD (in addition to anxiety), as it significantly lowered total duration in light (Example 7, FIG. 7B), reduced repetitive behaviors, including grooming, digging, and marble burying (Example 8, FIGS. 8A-C), increased ultrasonic vocalization frequency and duration (Example 9, FIGS. 9A-B), and lowered fecal output (Example 10, FIG. 10). Accordingly, it is contemplated that inhibiting 4EP (and therefore 4EPS) synthesis in the gut bacteria, for example, by culturing a genetically engineered *B. ovatus* comprising a loss-of-function mutation in BO1194 and/or a genetically engineered *L. plantarum* comprising a loss-of-function mutation in PAD in accordance with some embodiments herein can inhibit (e.g., reduce, or completely block or prevent) production of 4EPS in a mammal in need thereof. The inhibition of 4EP (and 4EPS) synthesis can ameliorate, reduce the likelihood, and/or delay the onset of one or more symptoms associated with ASD and/or anxiety in the mammal. Additionally, the polyphenols quercetin and curcumin were shown to inhibit sulfation of 4EP, and thus inhibit the production of 4EPS (Example 11, FIGS. 11A-E). Accordingly, it is further contemplated that a composition comprising quercetin and/or curcumin is useful for inhibiting the production of 4EPS in a subject in need thereof.

It is contemplated that decreasing or inhibiting the production of 4EPS (or one of its precursors, such as 4EP, 4-vinylphenol, and/or p-coumaric acid) in accordance with some embodiments herein can ameliorate, delay the onset of, or lower the likelihood of symptoms associated with anxiety and/or ASD in a mammal in need thereof, for example a human. As decreasing or inhibiting production of a precursor of 4EPS is also understood to decrease or inhibit 4EPS production, it will be appreciated herein that organisms referred to "deficient in 4EPS" production (or variations of this root term) may be deficient in the production of a precursor of 4EPS, and/or in EPS itself. Furthermore, it is appreciated that an organism deficient in producing a precursor of EPS (e.g., p-coumaric acid, 4-vinylphenol, and/or 4EP), will also be deficient in producing 4EPS. Thus, in some embodiments, the production of 4EPS can be inhibited by mutating *B. ovatus* and/or *L. plantarum* genes in the pathway that synthesizes 4EPS. In some embodiments, a composition or product combination comprising, consisting essentially of, or consisting of genetically engineered *B. ovatus* bacteria and/or genetically engineered *L. plantarum* bacteria deficient in producing 4EPS (for example *B. ovatus* comprising a loss-of-function mutation in a gene encoding BO1194, and/or *L. plantarum* comprising a loss-of-function in a gene encoding phenolic acid decarboxylase (PAD)) is useful for reducing or inhibiting the production of 4EPS upon administration to a subject in need thereof. As used herein a "loss-of-function" (including variations of this root term) encompasses both partial loss-of-function (e.g., a hypomorphic mutation), as well as complete loss-of-function (e.g., a null mutation, such as a phenotypic null mutation, or a deletion of the relevant gene). Accordingly, it is contemplated that bacteria "deficient" in producing 4EPS, as referred to herein (including variations of this root term), can completely fail to produce 4EPS, or can produce 4EPS at a reduced level and/or reduced rate compared to corresponding wild-type bacteria. Furthermore, in some embodiments, a composition or product combination comprising, consisting essentially of, or consisting of a polyphenol such as quercetin and/or curcumin is useful for inhibiting the production of 4EPS in a subject in need thereof. In some embodiments, a composition or product combination comprises the genetically engineered *B. ovatus* and/or *L. plantarum* bacteria deficient in producing 4EPS (as described herein) and the polyphenol such as quercetin and/or curcumin. The composition or product combination can be used to inhibit the production of 4EPS in a subject in need thereof. The composition or product combination can be further useful for ameliorating, delaying the onset of, and/or reducing the likelihood of one or more symptoms associated with anxiety and/or ASD in the subject.

Compositions and/or Product Combinations Comprising Genetically Engineered *Bacteroides ovatus* and/or *Lactobacillus plantarum* (and/or a Polyphenol)

It is reported herein that *Bacteroides ovatus* deficient in genes for 4EP synthesis can colonize the gut of subjects with anxiety and/or ASD, produce lower 4EPS levels, and ameliorate symptoms associated with anxiety and/or ASD (See Examples 3, and 5-10, and FIGS. 3C and 5A-10). As

*Lactobacillus plantarum* also participates in the 4EP synthesis, it is further contemplated that *Lactobacillus plantarum* deficient in genes for 4EP synthesis can also colonize the gut of subjects with anxiety and/or ASD, produce lower 4EPS levels, and ameliorate symptoms associated with anxiety and/or ASD. Some embodiments include a composition or product combination comprising, consisting essentially of, or consisting of a genetically engineered *Bacteroides ovatus* comprising a loss-of-function mutation in a gene encoding BO1194, and/or a genetically engineered *Lactobacillus plantarum* comprising a loss-of function mutation in a gene encoding phenolic acid decarboxylase (PAD). It noted that in some embodiments, the components of any of the noted compositions can be provided separately as "product combinations" in which the components are provided in two or more precursor compositions, which can either be combined to form the final composition (e.g., mix bacteria with another bacteria and/or one or more polyphenol to arrive at a final composition comprising a mixture of bacteria and/or polyphenol) or used in conjunction to achieve an effect similar to the single composition (e.g., administer bacteria and one or more polyphenols to a subject simultaneously or sequentially). In some embodiments, the composition or product combination comprises an amount of the genetically engineered *Bacteroides ovatus* and/or *Lactobacillus plantarum* sufficient to colonize the gut of, and reduce or inhibit 4EPS production in a mammalian subject. In some embodiments, the composition or product combination further comprises a polyphenol such as quercetin and/or curcumin. In some embodiments, the composition or product combination comprises an amount of the polyphenol sufficient to reduce or inhibit 4EPS production in the subject. In some embodiments, the composition or product combination further comprises one or more *Bacteroides* bacteria (other than *B. ovatus*), such as *B. fragilis, B. thetaiotaomicron,* or a combination of *B. fragilis* and *B. thetaiotaomicron*. In some embodiments, any composition or product combination as described herein is for use in ameliorating, delaying the onset of, or reducing the likelihood of one or more symptoms associated with anxiety and/or ASD in a subject having anxiety or ASD, or at risk of having anxiety or ASD. In some embodiments, any composition or product combination as described herein is for use in ameliorating, delaying the onset of, or reducing the likelihood of one or more symptoms associated with anxiety in a subject having anxiety or at risk of having anxiety. In some embodiments, the use is for ameliorating, delaying the onset of, or reducing the likelihood of anxiety. In some embodiments, the use is for ameliorating, delaying the onset of, or reducing the likelihood of anxiety or one or more disorders associated with anxiety, for example, depression, chronic illness, eating disorders, headaches, hoarding disorder, irritable bowel syndrome, sleep disorders, substance use disorders, attention deficit/hyperactive disorders, chronic pain, and/or fibromyalgia. In some embodiments, any composition or product combination as described herein is for use in ameliorating, delaying the onset of, or reducing the likelihood of one or more symptoms associated with ASD in a subject having ASD or at risk of having ASD. Example symptoms associated with ASD include, but are not limited to repetitive behavior, hyperactivity, and communication disorders. Anxiety (and its associated symptoms) can also be associated with ASD, and anxiety itself can sometimes be considered symptomatic of ASD. In some embodiments, the composition or product combination is for use in ameliorating, delaying the onset of, or reducing the likelihood of anxiety in a subject having anxiety or at risk of having anxiety.

In some embodiments, the subject is identified and/or selected as being within a class of subjects that should receive the composition or product combination. In some embodiments, the subject is determined to have one or more one or more symptoms of anxiety (e.g., elevated startle, or restlessness) or a disorder related to anxiety (e.g., depression, chronic illness, eating disorders, headaches, hoarding disorder, irritable bowel syndrome, sleep disorders, substance use disorders, attention deficit/hyperactive disorders, chronic pain, fibromyalgia), or one or more symptoms of ASD (e.g., repetitive behaviors, anxiety, and/or deficient communication behavior), or a level of 4EPS in a sample of the subject is higher than that of a non-anxiety and/or non-ASD (as applicable) control subject, thus selecting the subject as being within a class of subjects that should receive the composition. In some embodiments, the subject has ASD, anxiety, and/or on or more of depression, chronic illness, eating disorders, headaches, hoarding disorder, irritable bowel syndrome, sleep disorders, substance use disorders, attention deficit/hyperactive disorders, chronic pain, and fibromyalgia. In some embodiments, the sample of the subject comprises, consists essentially of, or consists of urine or serum. In some embodiments, the composition is for use in ameliorating, delaying the onset of, or reducing the likelihood of one or more symptoms associated with ASD and/or anxiety in a subject having anxiety or at risk of having anxiety. The use can comprise inhibiting production of 4-ethylphenol (4EP) and/or 4-ethylphenyl sulfate (4EPS) in the subject, so as to ameliorate, delay the onset of, or decrease the likelihood of the symptoms associated with ASD and/or anxiety. In some embodiments, the composition is for use in ameliorating, delaying the onset of, or reducing the likelihood of one or more symptoms associated with anxiety in a subject having anxiety or at risk of having anxiety, and the use comprises inhibiting production of 4-ethylphenol (4EP) and/or 4-ethylphenyl sulfate (4EPS) in the subject, so as to ameliorate, delay the onset of, or decrease the likelihood of the symptoms associated with anxiety. In some embodiments, the composition is for use in ameliorating, delaying the onset of, or reducing the likelihood of one or more symptoms associated with ASD in a subject having ASD or at risk of having ASD, and the use comprises inhibiting production of 4-ethylphenol (4EP) and/or 4-ethylphenyl sulfate (4EPS) in the subject, so as to ameliorate, delay the onset of, or decrease the likelihood of the symptoms associated with ASD. In some embodiments, the subject is a mammal. In some embodiments, the mammal is a human.

It is shown herein that polyphenols such as quercetin and/or curcumin can inhibit or reduce the production of 4EPS by inhibiting the sulfation of 4EP (See Example 11). Further, it is reported herein that 4EPS can induce anxiety (See, e.g., Example 4), but that reducing or inhibit 4EPS production can ameliorate, delay the onset of, or reduce the likelihood of anxiety (See Examples 5-10). As such, some embodiments include a composition comprising a polyphenol such as quercetin and/or curcumin) for use in ameliorating, delaying the onset of, or decreasing the likelihood of anxiety and/or ASD in a subject. In some embodiments, the use comprises inhibiting or reducing production of 4EPS in the subject, thus ameliorating, delaying the onset of, or decreasing the likelihood of anxiety and/or ASD. In some embodiments the composition or product combination comprises an amount of polyphenol such as quercetin and/or curcumin sufficient to inhibit or reduce production of 4EPS in the subject. In some embodiments, the subject is selected as being within a class of subjects that should receive the composition. For example, in some embodiments, the subject can be determined to have anxiety, and/or ASD, and/or a level of 4EPS in a sample of the subject can be determined to be higher than those of a non-anxiety and/or non-ASD control subject. Based on any of these (or any combination of two or more of these), the subject can thus be selected as being within a class of subjects that should receive the composition. In some embodiments, the composition or product combination further comprises genetically engineered *Bacteroides ovatus* comprising a loss-of-function mutation in a gene encoding BO1194 as described herein, and/or a genetically engineered *Lactobacillus plantarum* comprising a loss-of function mutation in a gene encoding phenolic acid decarboxylase (PAD) as described herein.

In some embodiments, the composition or product combination comprises, consists essentially of, or consists of genetically engineered *Bacteroides ovatus* comprising a loss-of-function mutation in a gene encoding BO1194, and/or a genetically engineered *Lactobacillus plantarum* comprising a loss-of function mutation in a gene encoding phenolic acid decarboxylase (PAD). "Genetically engineered" has its customary and ordinary meaning as understood by one of skill in the art in view of this disclosure. It refers to an organism (such as a bacterial strain) comprising one or more induced mutations or genetic modifications such as deletions, insertions, frameshifts, and/or rearrangements, and/or comprising on or more genetic constructs (such as a plasmid, array, or artificial chromosome) so that the organism differs from wild-type. In some embodiments, the composition or product combination comprises, consists essentially of, or consists of genetically engineered *Bacteroides ovatus* comprising a loss-of-function mutation in a gene encoding BO1194. In some embodiments, the composition or product combination comprises, consists essentially of, or consists of genetically engineered *Lactobacillus plantarum* comprising a loss-of function mutation in a gene encoding phenolic acid decarboxylase (PAD). In some embodiments, the composition or product combination comprises, consists essentially of, or consists of genetically engineered *Bacteroides ovatus* comprising a loss-of-function mutation in a gene encoding BO194, and genetically engineered *Lactobacillus plantarum* comprising a loss-of function mutation in a gene encoding phenolic acid decarboxylase (PAD). By way of example, the loss-of-function mutation in either or both genes can comprise a deletion, insertion, substitution, rearrangement, or frameshift. In some embodiments, the genetically engineered *Bacteroides ovatus* comprising the loss-of-function mutation in the gene encoding BO1194, and the genetically engineered *Lactobacillus plantarum* comprising the loss-of function mutation in the gene encoding PAD can be together in a single composition. In some embodiments, the genetically engineered *Bacteroides ovatus* comprising the loss-of-function mutation in the gene encoding BO1194, and the genetically engineered *Lactobacillus plantarum* comprising the loss-of function mutation in a gene encoding PAD can be in separate compositions that are part of the same product combination. In some embodiments, the composition or product combination comprises the *Bacteroides ovatus* comprising the loss-of-function mutation in the gene encoding BO1194, and the loss-of-function mutation comprises a deletion, insertion, substitution, rearrangement, or frameshift. In some embodiments, the composition or product combination comprises the *Lactobacillus plantarum* comprising the loss-of-function mutation in the gene encoding PAD, and the loss-of-function mutation comprises a deletion, insertion, substitution, rearrangement, or frameshift. In some embodiments, the composition or product combination comprises the *Bacteroides ovatus* comprising the loss-of-function mutation in the gene encoding BO1194 and the *Lactobacillus plantarum* comprising the loss-of-function mutation in the gene encoding PAD, and each loss-of-function mutation comprises a deletion, insertion, substitution, rearrangement, or frameshift. The loss of function mutations in the genes encoding BO1194 and PAD in the respective *Bacteroides ovatus* and *Lactobacillus plantarum* can be of the same type (e.g., a deletion of each gene), or of different types (e.g., a deletion of BO1194 and a frameshift in PAD). A non-limiting example wild-type sequence of *Bacteroides ovatus* BO1194 suitable for some embodiments herein (for example, as a reference from which mutations can be made) is provided as SEQ ID NO: 1. A non-limiting example wild-type sequence of *Lactobacillus plantarum* PAD suitable for some embodiments herein (for example, as a reference from which mutations can be made) is provided as SEQ ID NO: 2. Also, a wild-type *B. subtilis* PAD, an ortholog of *B. ovatus* PAD that has been experimentally validated to function in 4EP synthesis (See Example 3) is provided as SEQ ID NO: 5, and it is contemplated that in some embodiments herein, the *L. plantarum* gene encoding PAD is an ortholog of *B. subtilis* PAD. In some embodiments, a mutant BO1194 sequence comprises a deletion of at least 1 nucleotide, for example, 1, 2, 3, 4, 5, 6, 7, 8, 9, 10, 11, 12, 13, 14, 15, 6, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, or 150 nucleotides of SEQ ID NO: 1, including ranges between any two of the listed values, for example, 1-150, 2-150, 5-150, 10-150, 50-150, 1-100, 2-100, 5-100, 50-100, 1-50, 2-50, 5-50, 10-50, 1-20, 2-20, 5-20, 10-20, 1-10, 2-10, or 5-10. In some embodiments, a mutant BO1194 sequence comprises a point mutation in SEQ ID NO: 1, for example an insertion of a premature stop codon in-frame. In some embodiments, a mutant BO1194 sequence comprises a point mutation in SEQ ID NO: 1, for example a frameshift mutation, for example the insertion or deletion of a quantity of nucleotides that is not a multiple of 3 (e.g., insertion or deletion of 1, 2, 4, 5, 7, 8, 10, 11, 13, 14, 16, 17, 19, 20, 22, 23, 25, 26, 28, 29, 31, 32, 34, 35, 37, 38, 40, 41, 43, 44, 46, 47, 49, or 50 nucleotides). In some embodiments, a mutant PAD sequence comprises a deletion of at least 1 nucleotide, for example, 1, 2, 3 4, 5, 6, 7, 8, 9, 10, 11, 12, 13, 14, 15, 6, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 105, 110, 115, 120, 125, 130, 135, 140, 145, or 150 nucleotides of SEQ ID NO: 2, including ranges between any two of the listed values, for example, 1-150, 2-150, 5-150, 10-150, 50-150, 1-100, 2-100, 5-100, 50-100, 1-50, 2-50, 5-50, 10-50, 1-20, 2-20, 5-20, 10-20, 1-10, 2-10, or 5-10. In some embodiments, a mutant PAD sequence comprises a point mutation in SEQ ID NO: 2, for example an insertion of a premature stop codon in-frame. In some embodiments, a mutant PAD sequence comprises a point mutation in SEQ ID NO: 2, for example a frameshift mutation, for example the insertion or deletion of a quantity of nucleotides that is not a multiple of 3 (e.g., insertion or deletion of 1, 2, 4, 5, 7, 8, 10, 11, 13, 14, 16, 17, 19, 20, 22, 23, 25, 26, 28, 29, 31, 32, 34, 35, 37, 38, 40, 41, 43, 44, 46, 47, 49, or 50 nucleotides). The genetically engineered *B. ovatus* comprising the mutation in BO1194, and/or the genetically engineered *L. plantarum* comprising the mutation in PAD can be made using any number of molecular biology techniques, for example homologous recombination with a construct comprising the mutant sequence, use of a CRISPR system, or mutagenesis in conjunction with selection or screening. It is noted that the genetically engineered *B. ovatus* and genetically engineered *L. plantarum* of product combinations and/or compositions of some embodiments are not necessarily constructed using the same techniques. Examples of techniques suitable for making genetically engineered bacteria such as genetically engineered *B. ovatus* and/or *L. plantarum* in accordance with compositions and product combinations as described herein are provided in Green and Sambrook, Molecular Cloning: A Laboratory Manual. Cold Spring Harbor Laboratory Press, N.Y., (4th Edition) (2012), which is hereby incorporated by reference in its entirety. In some embodiments, the genetically engineered *B. ovatus* and/or *L. plantarum* comprises a synthetic chromosome or portion thereof comprising the relevant mutation(s) in BO194 and/or PAD.

In some embodiments, the genetically engineered *Bacteroides ovatus* and/or genetically engineered *Lactobacillus plantarum* (and/or the pair of *B. ovatus* and *L. plantarum*) of the composition or product combination is deficient in the production of 4EP, 4EPS, or at least on intermediate shown in FIG. 3A, for example, p-coumaric acid, and/or 4-vinylphenol. In some embodiments, the genetically engineered *Bacteroides ovatus* is deficient in the production of p-coumaric acid. In some embodiments, the genetically engineered *Bacteroides ovatus* and/or genetically engineered *Lactobacillus plantarum* (and/or the pair of *B. ovatus* and *L. plantarum*) is deficient in the production of 4-vinylphenol.

It is shown herein that *Bacteroides ovatus* and *Lactobacillus plantarum* function together as a pair in the synthesis of 4EPS (See, e.g., Example 3). Accordingly, in some embodiments, it is contemplated that to reduce or inhibit 4EPS production, the composition or product combination comprises a genetically engineered *Bacteroides ovatus* as described herein, but is free or substantially free of *Lactobacillus plantarum*. In some embodiments, to reduce or inhibit 4EPS production, the composition or product combination comprises a genetically engineered *Lactobacillus plantarum* as described herein, but is free or substantially free of *Bacteroides ovatus*. As used herein, "substantially free" and variations of this root term has its customary and ordinary meaning as understood by one of skill in the art in view of this disclosure. It refers to a composition and/or product combination (which may be for a use or a method as described herein) having no more than trace amounts of a substance (e.g., a bacteria such as *Bacteroides ovatus* or *Lactobacillus plantarum*), and/or the amount or presence of the substance having no appreciable effect (e.g., behavioral effect) on the subject. For example, in some embodiments, a composition, product combination, use, and/or method substantially free of a bacteria comprises no more than about $10^6$ colony forming units (cfu) of that bacteria, for example no more than $10^6$ cfu, $10^5$ cfu, $10^4$ cfu, $10^3$ cfu, $10^2$ cfu, or 10 cfu. In some embodiments, the composition, product combination, use, and/or method comprises a genetically engineered *Bacteroides ovatus* comprising a loss-of-function mutation in BO1194 as described herein, and comprises no more than $10^6$ cfu, $10^5$ cfu, $10^4$ cfu, $10^3$ cfu, $10^2$ cfu, or 10 cfu of *Lactobacillus plantarum*. In some embodiments, the composition, product combination, use, and/or method comprises a genetically engineered *Lactobacillus plantarum* comprising a loss-of-function mutation in PAD as described herein, and comprises no more than $10^6$ cfu, $10^5$ cfu, $10^4$ cfu, $10^3$ cfu, $10^2$ cfu, or 10 cfu of *Bacteroides ovatus*.

In some embodiments, the composition, product combination, use, and/or method comprises an amount of bacteria (e.g., genetically engineered *Bacteroides ovatus* and/or genetically engineered *Lactobacillus plantarum* as described herein) sufficient to establish a colony (e.g., a colony that persists for at least 1, 2, 3, 4 or more weeks post-inoculation) in the gut of a human subject when administered in a standard manner for microbiome transplant, probiotic treatment or equivalent procedures. Such an amount of bacteria may be referred to herein as an "inoculum." In some embodiments, the amount of bacteria in any of the compositions, product combinations, uses, or methods described herein includes at least $10^4$ cfu, for example at least $10^4$, $10^5$, $10^6$, $10^7$, $10^8$, $10^9$, $10^{10}$, $10^{11}$, $10^{12}$, or $10^{13}$ cfu, including ranges between any of the listed values, for example $10^4$-$10^8$ cfu, $10^4$-$10^9$ cfu, $10$-$10^{10}$ cfu, $10^4$-$10^{11}$ cfu, $10^4$-$10^{12}$ cfu, $10^4$-$10^{12}$ cfu, $10^5$-$10^8$ cfu, $10^5$-$10^9$ cfu, $10^5$-$10^{10}$ cfu, $10^5$-$10^{11}$ cfu $10^5$-$10^{12}$ cfu, $10^5$-$10^{12}$ cfu, $10^6$-$10^8$ cfu, $10^6$-$10^9$ cfu, $10^6$-$10^{10}$ cfu, $10^6$-$10^{11}$ cfu, $10^6$-$10^{12}$ cfu, $10^6$-$10^{12}$ cfu, $10^7$-$10^8$ cfu, $10^7$-$10^9$ cfu, $10^7$-$10^{10}$ cfu, $10^7$-$10^{11}$ cfu, $10^7$-$10^{12}$ cfu, $10^7$-$10^{12}$ cfu, $10^9$ cfu, $10^8$-$10^{10}$ cfu, $10^8$-$10^{11}$ cfu, $10^8$-$10^{12}$ cfu, or $10^8$-$10^{12}$ cfu. In some embodiments, the composition, product combination, use, and/or method comprises a log phase (e.g., at 37° C.) of bacteria for administration to the subject. In some embodiments, the composition, product combination, use, and/or method comprises a stationary phase (e.g., at 37° C.) of bacteria for administration to the subject. In some embodiments, the bacteria of the composition, product combination, use, and/or method are isolated bacteria. In some embodiments, the composition or product combination comprises at least $10^4$ cfu of the genetically engineered *Bacteroides ovatus*. In some embodiments, the composition or product combination comprises at least $10^4$ cfu, $10^5$ cfu, $10^6$ cfu, $10^7$ cfu, or $10^8$ cfu of the genetically engineered *Lactobacillus plantarum*. In some embodiments, the composition or product combination comprises at least $10^4$ cfu of the genetically engineered *Bacteroides ovatus* and at least $10^4$ cfu of the genetically engineered *Lactobacillus plantarum* (e.g., at least $10^4$ cfu, $10^5$ cfu, $10^6$ cfu, $10^7$ cfu, or $10^8$ cfu of either or both bacteria).

In some embodiments, any of the compositions and/or product combinations described herein (including those for uses and/or methods as described herein) comprises a pharmaceutically acceptable carrier or excipient. "Pharmaceutically acceptable" carriers have their ordinary and customary meaning as would be understood by one of skill in the art in view of this disclosure, and include ones which are nontoxic to the cell or mammal being exposed thereto at the dosages and concentrations employed. Example "Pharmaceutically acceptable" carriers in accordance with methods and uses and compositions and product combinations herein can comprise, but not limited to, organic or inorganic, solid or liquid excipients which is suitable for the selected mode of application such as oral application and/or rectal administration, and administered in the form of a conventional pharmaceutical preparation, such as solid such as tablets, granules, powders, capsules, and liquid such as solution, emulsion, suspension and the like. Often the physiologically acceptable carrier is an aqueous pH buffered solution such as phosphate buffer or citrate buffer. The physiologically acceptable carrier may also comprise one or more of the following: antioxidants including ascorbic acid, low molecular weight (less than about 10 residues) polypeptides, proteins, such as serum albumin, gelatin, immunoglobulins;

hydrophilic polymers such as polyvinylpyrrolidone, amino acids, carbohydrates including glucose, mannose, or dextrins, chelating agents such as EDTA, sugar alcohols such as mannitol or sorbitol, salt-forming counterions such as sodium, and nonionic surfactants such as and nonionic surfactants such as TWEEN™ surfactant, polyethylene glycol (PEG), and PLURONICS™ surfactant. Auxiliary, stabilizer, emulsifier, lubricant, binder, pH adjustor controller, isotonic agent and other conventional additives may also be added to the carriers. In some embodiments, the composition is formulated for oral administration, rectal administration, or oral and rectal administration. In some embodiments, the composition and/or product combination comprises, consists essentially of, or consists of a probiotic.

In some embodiments, the composition or product combination is formulated for oral or rectal administration to a mammalian subject. In some embodiments, the composition or product combination is selected from the group consisting of: a probiotic composition, a pharmaceutical composition, a dietary supplement, and a food, or a combination of two or more of the listed items. The compositions and/or product combinations of some embodiments herein are available in foods and dietary supplements (for example, but not limited to capsules, tablets, powders, and liquids). Non-limiting examples of foods containing probiotic include dairy products such as yogurt, fermented and unfermented milk, smoothies, butter, cream, hummus, kombucha, salad dressing, miso, tempeh, nutrition bars, and some juices and soy beverages. In some embodiments, the composition or product combination comprises a single microorganism.

Methods of Reducing and/or Inhibiting Production of 4-Ethylphenol (4EP) and/or 4-Ethylphenyl Sulfate (4EPS) in a Subject Some embodiments include methods of reducing and/or inhibiting production of 4-ethylphenol (4EP) and/or 4-ethylphenyl sulfate (4EPS) in a subject. In some embodiments, the method comprises administering an amount of a composition or product combination comprising genetically engineered *Bacteroides ovatus* and/or a genetically engineered *Lactobacillus plantarum* as described herein, and/or a polyphenol as described herein to a subject in need of reducing and/or inhibiting production of 4EP and/or 4EPS.

In some embodiments, a method of reducing or inhibiting production of 4-ethylphenol (4EP) and/or 4-ethylphenyl sulfate (4EPS) in a subject in need thereof, is described. The method can comprise administering to the subject a composition or product combination comprising a genetically engineered *Bacteroides ovatus* comprising a loss-of-function mutation in a gene encoding BO1194, and/or a genetically engineered *Lactobacillus plantarum* comprising a loss-of function mutation in a gene encoding phenolic acid decarboxylase (PAD). The method can comprise permitting the genetically engineered *Bacteroides ovatus* and/or *Lactobacillus plantarum* to proliferate in a gastrointestinal tract of the subject. Thus, production of 4EP and/or 4EPS is inhibited in the subject. It is contemplated that in accordance with embodiments described herein, any composition or product combination comprising (or consisting essentially of, or consisting of) genetically engineered *Bacteroides ovatus* and/or genetically engineered *Lactobacillus plantarum* as described herein can be administered to the subject in the method. In some embodiments, the genetically engineered *Bacteroides ovatus* and genetically engineered *Lactobacillus plantarum* are administered together in a single composition (e.g., a co-culture). In some embodiments, the genetically engineered *Bacteroides ovatus* and genetically engineered *Lactobacillus plantarum* are administered separately, for example at separate times, and/or via separate routes of administration.

The genetically engineered *Bacteroides ovatus* and/or genetically engineered *Lactobacillus plantarum* (or the pair of genetically engineered *Bacteroides ovatus* and genetically engineered *Lactobacillus plantarum*) can be deficient in one or more genes that encode products in the 4EPS synthetic pathway (See FIG. 3A), for example comprising a loss-of-function mutation in *Bacteroides ovatus* BO1194 and/or *Lactobacillus plantarum* PAD as described herein. Without being limited by theory, it is contemplated that proliferation of genetically modified *Bacteroides ovatus* and/or genetically engineered *Lactobacillus plantarum* deficient in the production of 4EP (and 4EPS) can inhibit production of 4EP and/or 4EPS (See, e.g., Examples 3, FIG. 3B), thus resulting in lower levels of 4EP and/or 4EPS in the host, or substantial or complete elimination of 4EP and/or 4EPS in the host. Furthermore, co-culturing genetically modified *B. ovatus* strains and *L. plantarum* strains collectively deficient in the 4EP (and therefore 4EPS) synthetic pathway alleviated symptoms of anxiety (See Examples 5-7, FIGS. 5A-7C), and further alleviated symptoms associated with ASD, for example, reducing repetitive behaviors, including grooming, digging, and marble burying (Example 8, FIGS. 8A-C), and improving communication behaviors, for example increasing ultrasonic vocalization frequency and duration (Example 9, FIGS. 9A-B). As the biosynthetic pathway of 4EP (and 4EPS) in *B. ovatus* and *L. plantarum* is described herein (See, e.g., Example 3) it is further contemplated that culturing other *B. ovatus, L. plantarum*, and/or pairs thereof comprising mutations in the 4EP (and 4EPS) biosynthetic pathway in accordance with some embodiments herein has similar effects in ameliorating, decreasing the likelihood, and/or delaying the onset of symptoms of ASD and/or anxiety. Thus, in some embodiments, the method results in amelioration, delay of onset, inhibition, or reduction in the likelihood of symptoms associated with anxiety and/or ASD. Thus, in some embodiments, the method results in amelioration, delay of onset, inhibition, or reduction in the likelihood of ASD, anxiety, and/or a disorder associated with anxiety as described herein. In some embodiments, reducing the levels of 4EP and/or 4EPS ameliorates, delays the onset of, or decreases the likelihood of anxiety in the subject.

Some embodiments include a method of reducing or inhibiting production of 4-ethylphenyl sulfate (4EPS) in a subject in need thereof. The method can comprise administering a polyphenol to the subject. It is shown herein that polyphenols can inhibit sulfation of 4EP into 4EPS (See. Example 11). Accordingly, the amount of polyphenol can be effective of reducing or inhibiting production of 4EPS in the subject. In some embodiments, the polyphenol comprises, consists essentially of, or consists of quercetin and/or curcumin. In some embodiments, reducing the levels of 4EP and/or 4EPS ameliorates, delays the onset of, or decreases the likelihood of a symptom associated with anxiety in the subject. In some embodiments, reducing the levels of 4EP and/or 4EPS ameliorates, delays the onset of, or decreases the likelihood of a symptom associated with anxiety ASD in the subject. In some embodiments, the method further comprises, prior to said administering, selecting the subject as being within a class of subjects that are in need of receiving the composition. The selecting can be as described herein. In some embodiments, the selecting comprises identifying the subject as having one or more symptoms associated with anxiety and/or ASD as described herein.

In some embodiments, ASD, or an ASD behavior, for example a deficient communication, vocalization, sensorimotor, anxiety, and/or repetitive behavior, or a combination of two or more of these is identified using standard diagnostic criteria, for example in the Diagnostic and Statistical Manual of Mental Disorders, Fourth Edition (DSM-4) or Fifth Edition (DSM-5). In some embodiments, the presence or absence of ASD in the subject is determined using a behavioral test, for example at least one of the Autism Behavior Checklist (ABC), Autism diagnostic Interview-Revised (ADI-R), childhood autism Rating Scale (CARS), and/or Pre-Linguistic Autism Diagnostic Observation Schedule (PL-ADOS). The behavioral test can include, but is not limited to, detecting the presence and/or extent of 1) preoccupation with one or more stereotyped and restricted patterns of interest that is abnormal in either intensity or focus, 2) inflexible adherence to specific, nonfunctional routines or rituals, c) stereotyped and repetitive motor mannerisms (such as hand flapping, finger flapping etc.), and/or d) persistent preoccupation with parts of objects. Non-limiting examples of behavior that can be included in a behavioral test and suggest a need for improving behavioral performance in the subject under the test include: a) sensory behaviors, including poor use of visual discrimination when learning, seems not to hear, so that a hearing loss is suspected, sometimes shows no "startle response" to loud noise", sometimes painful stimuli such as bruises, cuts, and injections evoke no reaction, often will not blink when bright light is directed toward eyes, covers ears at many sounds, squints, frowns, or covers eyes when in the presence of natural light, frequently has no visual reaction to a "new" person, stares into space for long periods of time; b) relating behaviors: frequently does not attend to social/environmental stimuli, has no social smile, does not reach out when reached for, non-responsive to other people's facial expressions/feelings, actively avoids eye contact, resists being touched or held, is flaccid when held in arms, is stiff and hard to held, does not imitate other children at play, has not developed any friendships, often frightened or very anxious, "looks through" people; c) body and object use behaviors: whirls self for long periods of time, does not use toys appropriately, insists on keeping certain objects with him/her, rocks self for long periods of time, does a lot of lunging and darting, flaps hands, walks on toes, hurts self by banging head, biting hand, twirls, spins, and bangs objects a lot, feel, smell, and/or taste objects in the environment, gets involved in complicated "rituals" such as lining things up, is very destructive; and d) language behaviors: does not follow simple commands given once, has pronoun reversal, speech is atonal, does not respond to own name when called out among two others, seldom says "yes" or "I", does not follow simple commands involving prepositions, gets desired objects by gesturing, repeats phrases over and over, cannot point to more than five named objects, uses 0-5 spontaneous words per day to communicate wants and needs, repeats sounds or words over and over, echoes questions or statements made by others, uses at least 15 but less than 30 spontaneous phrases daily to communicate, learns a simple task but "forgets" quickly, strong reactions to changes in routine/environment, has "special abilities" in one area of development, which seems to rule out mental retardation, severe temper tantrums and/or frequent minor tantrums, hurts others by biting, hitting, and/or kicking, does not wait for needs to be met, difficulties with toileting, does not dress self without frequent help, frequently unaware of surroundings, and may be oblivious to dangerous situations, prefers to manipulate and be occupied with inanimate things, and/or a developmental delay identified at or before 30 months of age. One of ordinary skill in the art would appreciate that the attending physician would know how to identify a subject in need of treatment disclosed herein.

In some embodiments, the subject in need of reducing and/or inhibiting production of 4EP and/or 4EPS has one or more symptoms associated with anxiety and/or ASD. Example symptoms associated with anxiety include restlessness and enhanced startle. Example symptoms associated with ASD include, but are not limited to repetitive behavior, hyperactivity, anxiety, and a communication disorder. In some embodiments, the subject in need has anxiety. In some embodiments, the subject in need has anxiety or a disorder related to anxiety, for example, depression, chronic illness, eating disorders, headaches, hoarding disorder, irritable bowel syndrome, sleep disorders, substance use disorders, attention deficit/hyperactive disorders, chronic pain, and fibromyalgia. In some embodiments, the subject in need has ASD.

In some embodiments, the method further comprises, prior to said administering, identifying and/or selecting the subject as being within a class of subjects that are in need of receiving the composition. For example, in some embodiments, the subject is selected as being within the class by identifying the subject as having anxiety. In some embodiments, the subject is selected as being within the class by detecting a level of 4EP and/or a level of 4EPS in a sample derived from the subject. A level of 4EP and/or 4EPS in the sample of the subject (for example a serum sample and/or urine sample) that is higher than in a non-ASD/non-anxiety control sample can indicated that the subject is in need of treatment. Levels of 4EP and/or 4EPS can be detected by a number of methods, for example mass spectrometry (e.g., liquid chromatography mass spectrometry, gas chromatography mass spectrometry), or immunoassays (e.g., ELISA, lateral flow assays).

Figure 9A:
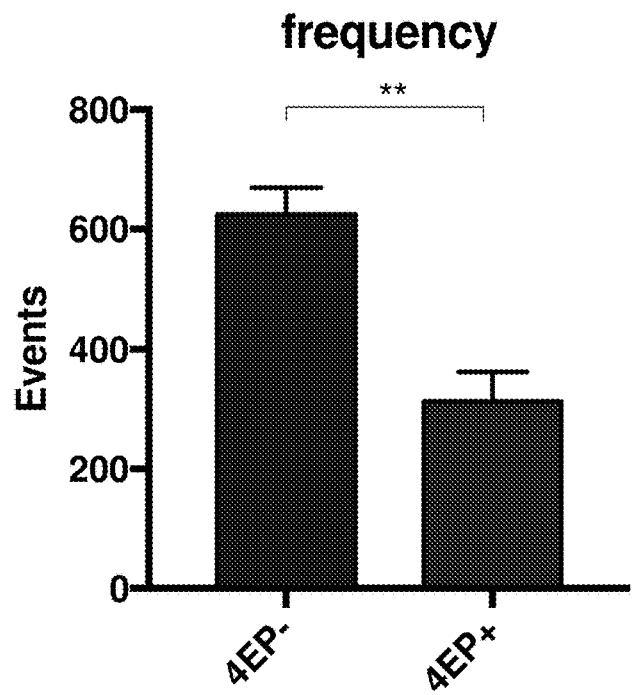
FIGS. 9A-B are a series of graphs showing results of an ultrasonic vocalization assay of some embodiments herein. Male mice were colonized with engineered bacteria either lacking or producing 4EP. Shown are frequency of ultrasonic vocalization events (FIG. 9A) and duration of ultrasonic vocalization events (FIG. 9B).
Figure 9B:
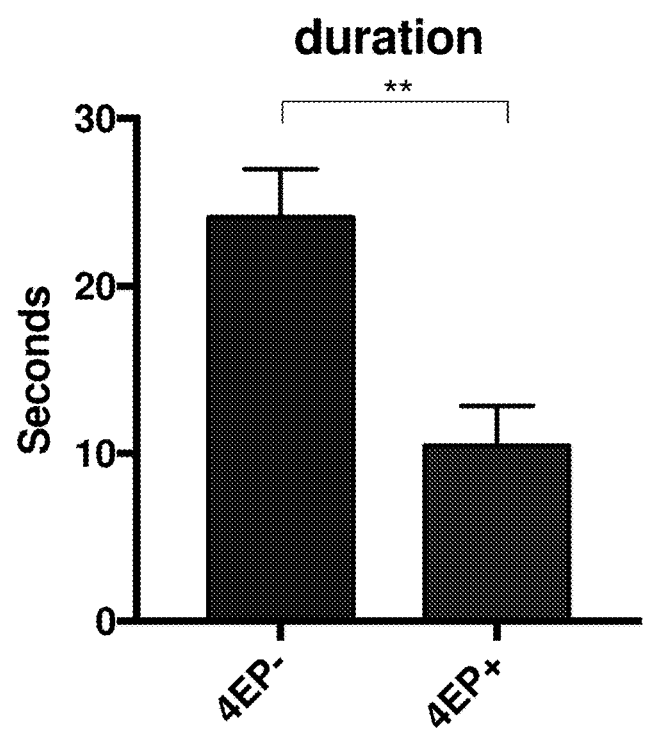

It is further observed herein that polyphenols can inhibit the production of 4EPS (See Example 9, FIGS. 9A-B). Accordingly, in some embodiments, any of the methods or uses described herein further comprises administering a polyphenol to the subject. In some embodiments, the polyphenol comprises, consists essentially of, or consists of quercetin and/or curcumin. In some embodiments, the polyphenol is part of the composition or product combination that comprises the genetically modified *B. ovatus* and/or *L. plantarum* as described herein. In some embodiments, the polyphenol is part of a single composition that comprises the genetically modified *B. ovatus* and/or *L. plantarum* as described herein and the polyphenol. In some embodiments, the polyphenol is administered together with the genetically modified *B. ovatus* and/or *L. plantarum*. In some embodiments, the polyphenol is administered separately from the genetically modified *B. ovatus* and/or *L. plantarum*, for example at different times, and/or via different routes of administration.

In some embodiments, the genetically engineered *Bacteroides ovatus* comprises a loss-of-function mutation in the gene encoding BO1194, and the loss-of-function mutation comprises a deletion, insertion, substitution, rearrangement, or frameshift. In some embodiments, the genetically engineered *Lactobacillus plantarum* comprises the loss-of-function mutation in the gene encoding PAD, and the loss-of-function mutation comprises a deletion, insertion, substitution, rearrangement, or frameshift.

It is noted that *Bacteroides ovatus* and *Lactobacillus plantarum* contributes as a pair to the synthesis of 4EP(S) (See Example 3). Accordingly, in order to reduce or inhibit synthesis of 4EP(S), it can be advantageous to administer only mutant *Bacteroides ovatus* as described herein in the absence of *Lactobacillus plantarum*, and/or to administer only mutant *Lactobacillus plantarum* as described herein in the absence of *Bacteroides ovatus*. In some embodiments of the method or use as described herein, the composition or product combination administered to the subject comprises the genetically engineered *Bacteroides ovatus*, and is substantially free of *Lactobacillus plantarum*. In some embodiments, the composition or product combination of the method or use comprises a genetically engineered *Bacteroides ovatus* comprising a loss-of-function mutation in BO1194 as described herein, and comprises no more than $10^6$ cfu, $10^5$ cfu, $10^4$ cfu, $10^3$ cfu, $10^2$ cfu, or 10 cfu of *Lactobacillus plantarum*. In some embodiments of the method or use as described herein, the composition or product combination administered to the subject comprises the genetically engineered *Lactobacillus plantarum*, and is substantially free of *Bacteroides ovatus*. In some embodiments, the composition or product combination of the method or use comprises a genetically engineered *Lactobacillus plantarum* comprising a loss-of-function mutation in PAD as described herein, and comprises no more than $10^6$ cfu, $10^5$ cfu, $10^4$ cfu, $10^3$ cfu, $10^2$ cfu, or 10 cfu of *Bacteroides ovatus*.

In some embodiments of the method or use as described herein, the subject is germ free. "Germ free" has its customary and ordinary meaning as understood by one of skill in the art in view of this disclosure. It can refer to a subject whose gut is substantially free of bacteria. For example, the subject can be germ free to facilitate recolonization of the subject's gut with a composition or product combination comprising genetically engineered *B. ovatus* and/or genetically engineered *Lactobacillus plantarum* in accordance with some embodiments herein.

In some embodiments, the method further comprises administering an antibiotic to the subject prior to administering the composition. The antibiotic can reduce a total quantity of gut bacteria of the subject by at least 80%, for example at least 80%, 85%, 90%, 95%, 96%, 97%, 98%, 99%, or 99.9%, including ranges between any of the listed values (e.g., 80%-99.9%, 80-95%, 85%-99.9%, and 85%-95%), prior to the administering of the composition. Example antibiotics that can be administered include, but are not limited to, the group consisting of: Amoxicillin, Amoxicillin/clavulanic acid (amoxicillin+clavulanic acid), Ampicillin, Benzathine benzylpenicillin, Benzylpenicillin, Cefalexin, Cefazolin, Cefixime, Cefotaxime, Ceftriaxone, Cloxacillin, Penicillin, Phenoxymethylpenicillin (penicillin V), Piperacillin/tazobactam, Procaine benzylpenicillin, Ceftazidime, Meropenem, Aztreonam, Imipenem/cilastatin, Amikacin, Azithromycin, Chloramphenicol, Ciprofloxacin, Clarithromycin, Clindamycin, Doxycycline, Erythromycin, Gentamicin, Metronidazole, Nitrofurantoin, Spectinomycin, Trimethoprim/sulfamethoxazole, Trimethoprim, Vancomycin, Clofazimine, Dapsone, Rifampicin, Ethambutol/isoniazid, Ethambutol/isoniazid/pyrazinamide/rifampicin, Ethambutol/isoniazid/rifampicin, Isoniazid, Isoniazid/pyrazinamide/rifampicin, Isoniazid/rifampicin, Pyrazinamide, Rifabutin, Rifampicin, Rifapentine, Amikacin, Bedaquiline, Capreomycin, Clofazimine, Cycloserine, Delamanid, Ethionamide, Kanamycin, Levofloxacin, Linezolid, Moxifloxacin, p-aminosalicylic acid, rifabutin, rifapentine, rifalazil, rifaximin and Streptomycin, or a combination of two or more of these antibiotics.

Additional Embodiments

Described herein are genes responsible for biosynthesis of 4EP, as well as bacterial species capable of producing it. No single organism has been identified as having entire 4EP synthetic pathway, but rather pairs that together produce 4EP in vitro and in vivo. In order to sustain high levels of 4EP for in vivo experiments, the naturally producing pair, *Bacteroides ovatus* and *Lactobacillus plantarum* has been engineered to overproduce the pathway (See Example 3). When germ-free mice are colonized with (1) *B. ovatus* overexpressing an important gene in the 4EP pathway, BO1194, along with (2) wild-type *L. plantarum*, the mice display an anxiety phenotype in the same behavior tests compared to the bacterial pair with a *B. ovatus* BO1194 mutant.

Some embodiments include drug development to target enzymes that produce 4EP.

Some embodiments include antibiotic development to specifically target bacteria involved in 4EP production and/or control.

Some embodiments include bacterial engineering to metabolize/degrade 4EP produced by other species.

Some embodiments include bacterial engineering to develop a strain that can invade health microbiota and outcompete 4EP-producing strains.

Some embodiments include drug development to inactivate 4EP/4EPS directly.

Some embodiments include targeting of host pathways involved in responding to 4EP/4EPS.

Some embodiments include treatment of a subject in need thereof using any of the techniques described herein for treating for diseases or disorders related to anxiety, such as: depression, chronic illness, eating disorders, headaches, hoarding disorder, irritable bowel syndrome, sleep disorders, substance use disorders, attention deficit/hyperactive disorders, chronic pain, and/or fibromyalgia.

EXAMPLES

Example 1: Levels and Effects of 4EPS in Mice

Levels of 4EPS in wild-type mice, and the maternal immune activation (MIA) mouse model of anxiety disorder and autism spectrum disorder (ASD) were measured.

The MIA mouse model promotes leakage of intestinal byproducts across the gut epithelium in the offspring of MIA mothers. The host is incapable of producing 4EP, but upon crossing the intestinal barrier in to host circulation, 4EP is modified with a sulfate group.

Relative quantification of 4EPS detected by GC/LC-MS showed that 4EPS is significantly altered in MIA mouse model of autism spectrum disorder ("P") and is restored by *B. fragilis* treatment ("P+BF"). n=8/group (FIG. 1A). In this analysis, 4EPS was 46-fold higher in MIA pups than controls. Accordingly, administering *B. fragilis* in accordance with some embodiments herein can reduce levels of 4EPS in a subject.

To measure effects of 4EPS on wild-type mice, the wild-type mice were injected intraperitoneally (i.p.) with saline or 30 mg/kg 4EPS potassium salt daily from 3 to 6 weeks of age. Anxiety-like behavior based on center duration (See FIG. 1B) and locomotor behavior (See FIG. 1C) were measured in the open field exploration assay. n=10/group. Furthermore, the potentiated startle reflex was measured in the pre-pulse inhibition (PPI) assay, and measurements were taken of startle (Vmax) (FIG. 1C) and PPI % (FIG. 1D). n=10/group. These data show that administering 4EPS significantly increased anxiety behaviors in wild-type mice.

Example 2: EPS Levels in and Effects in Human Children Samples

Figure 2B:
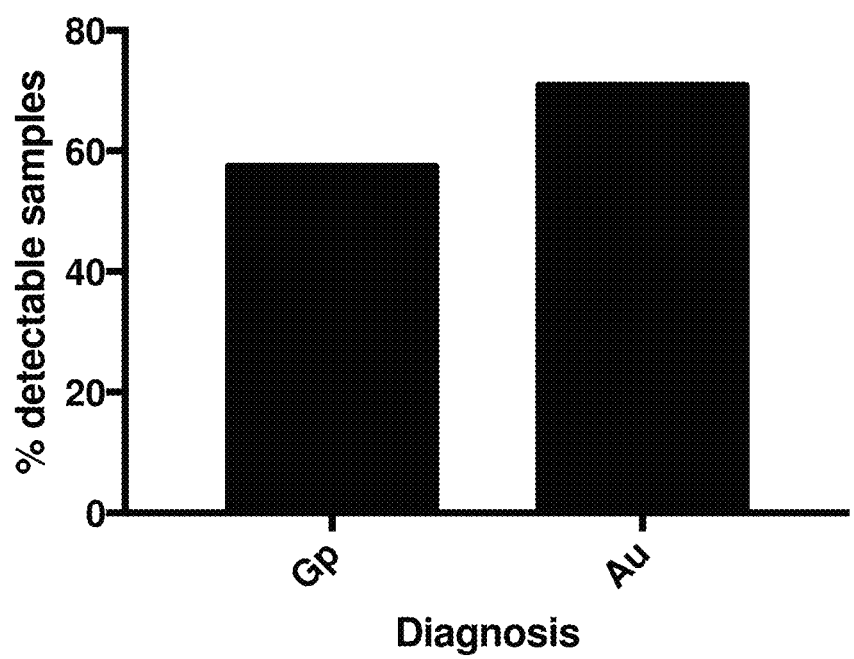
Figure 2C:
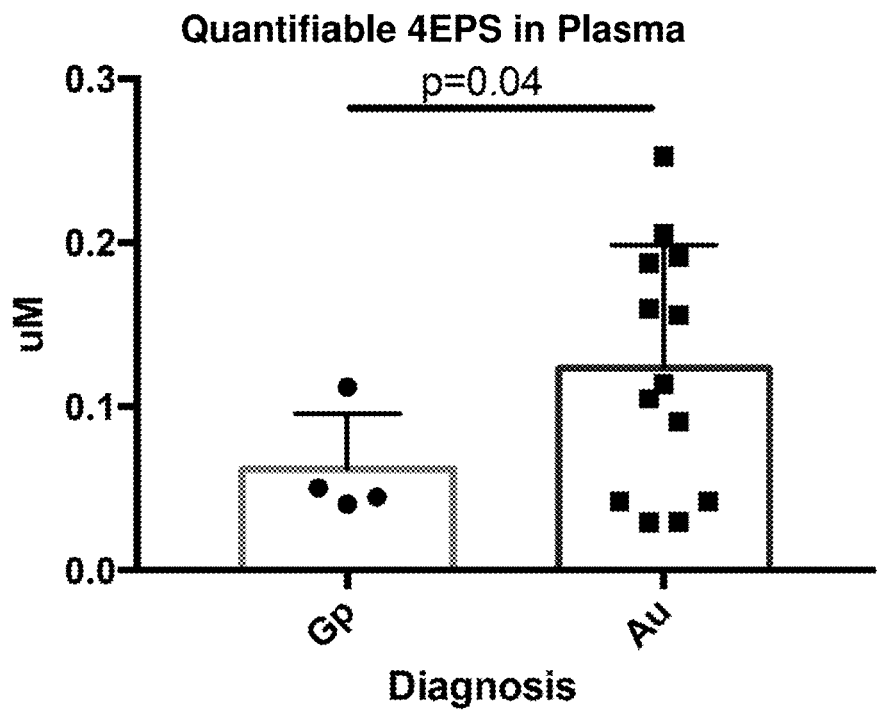
Figure 2D:
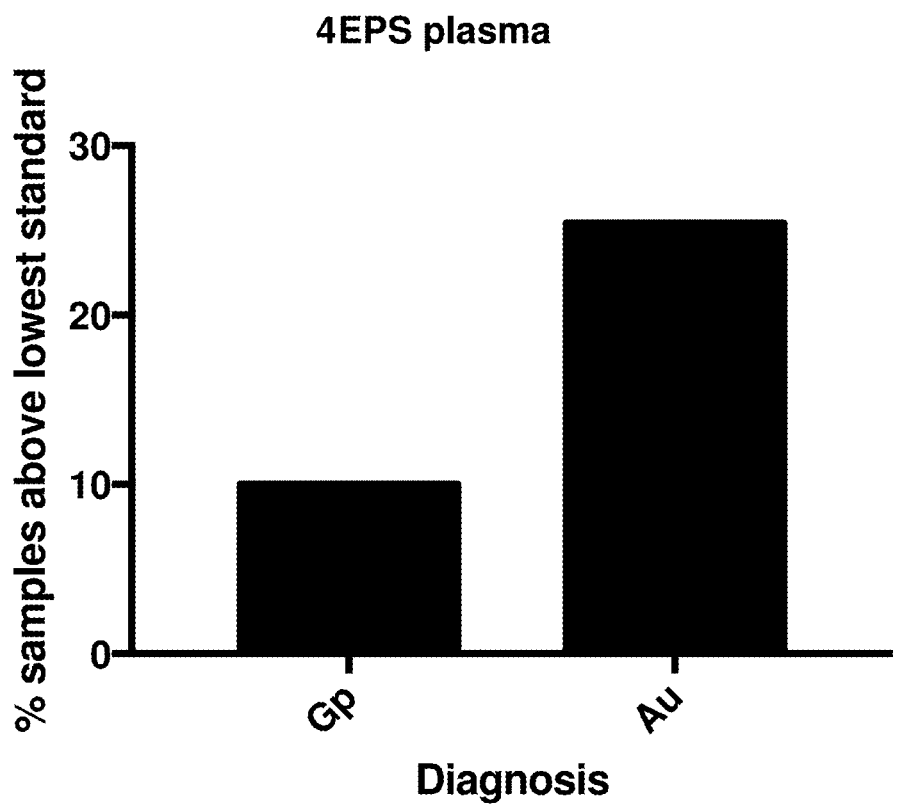

Human plasma from ASD and neurotypical children from the general population was analyzed by Liquid Chromatography Mass Spectrometry (LC/MS) for 4EPS. As shown in FIG. 2A, 4EPS levels were quantitated using a 4EPS standard curve. FIG. 2B shows that the percent of total samples in which 4EPS was detectable from ASD and general population children. Additionally, samples above the lowest standard in the standard curve are plotted, and the ASD population had higher levels of 4EPS in plasma than the general population (FIG. 2C). Another analysis made was the percent of total samples in which the 4EPS level was higher than lowest standard (FIG. 2D). The ASD population had a greater percentage of samples above the lowest standard (FIG. 2D). AU=Autistic, GP=general population

Example 3: 4EP(S) biosynthesis and genetic engineering of bacteria

The biosynthetic pathway of 4EP in *Bacteroides ovatus* and *Lactobacillus plantarum* was determined herein, and is summarized in FIG. 3A. The pathway involves synthetic steps in two different bacteria, *Bacteroides ovatus* and *Lactobacillus plantarum*, which together produce 4EP. In *Bacteroides ovatus*, BO119 converts tyrosine to p-coumaric acid. In *Lactobacillus plantarum*, PAD converts the p-coumaric acid to 4-vinylphenol. Also in *Lactobacillus plantarum*, the 4-vinylphenol is converted into 4EP.

It was shown that co-culturing of engineered *B. ovatus* and *L. plantarum* produces 4EP in vitro and in vivo. Genetically modified *B. ovatus* was generated in order to modulate 4EPS production and confirm the contributions of individual genes to the pathway.

PAD catalyzes decarboxylation of p-coumaric acid to produce 4-vinylphenol. BACOVA_01194 is involved in the biosynthesis of p-coumaric acid. These genes were considered as candidates for being involved in the synthesis of 4EP, and were tested, among other candidates, by constructing loss-of-function mutants and overexpression constructs. Approximately 20 *L. plantarum* mutants were also constructed in an attempt to ascertain *L. plantarum* genes involved in the final step of the pathway, conversion of 4-vinylphenol to 4EP (See FIG. 3A), but the *L. plantarum* genes involved in this final step were not identified as of the time of filing.

To construct mutant *B. ovatus* bacteria, *B. ovatus* ATCC 8483 ΔBAVOVA_03071 (tdk) was used for a parent strain.

For overexpression studies, chromosomal insertions were generated of both the native BACOVA_01194 gene (SEQ ID NO: 1), and the genes expressing the enzyme PAD (SEQ ID NO: 5) from *Bacillus subtilis*. Both genes (BCAOVA_1194 and PAD) were inserted in tandem, using the same plasmid, pNBU2 (SEQ ID NO: 3). This construct confers erythromycin resistance as well.

To construct the mutant *B. ovatus* deleted for BO1194, the following protocol was used. All PCR amplification was conducted using PrimeSTAR Max DNA polymerase (Takara Bio) according to the manufacturer's instructions. Sequences of primers were shown in Table 1. A double-crossover recombination method previously described was used (Koropatkin et. al., 2008). Briefly, ~1 kb DNA fragments corresponding to the upstream and downstream regions of the target gene were amplified followed by restriction digestion. These digested fragments were ligated into the suicide plasmid pExchange-tdk using T4 DNA ligase (New England Bio). *Escherichia coli* S17-1λ pir competent cells were transformed with the ligated plasmid was transformed into by electroporation and transformants were confirmed by PCR. The positive clone harboring ligated plasmid was cultivated and the plasmid was prepared. It was further verified by sequencing. Both *B. ovatus* Δtdk and *E. coli* 517-1λ pir harboring the plasmid were cultivated and the cells were harvested. The cell pellets were washed with PBS to remove residual antibiotics and combined them in TYG medium. The suspension was plated on BHI-blood agar medium without any antibiotics and grown aerobically at 37° C. for 1 day. The bacterial biomass was scraped up and re-suspended in TYG medium. The suspension was then plated on BHI-blood agar medium supplemented with erythromycin and gentamicin and single-crossover integrants were selected. These strains cultured in TYG medium overnight and plated on BHI-blood agar medium supplemented with FUdR. The deletion mutant was screened by PCR amplification and further verified by sequencing. Accordingly, *B. ovatus* comprising a loss-of-function mutation in accordance with some embodiments herein was constructed.

For co-culture, *B. ovatus* strains and *L. plantarum* were cultivated anaerobically in TYG (tryptone-yeast extract-glucose) broth and MRS broth (BD), respectively overnight at 37° C. and the cells were harvested followed by minimal medium (MM) wash. The cell pellet was re-suspended with MM containing 0.5 mg/ml tyrosine to be OD600 of 1.0 and combined two strains in the same tube. After 1 day incubation, samples for HPLC analysis were prepared.

Multiple rounds of engineering were done to increase the yield of 4EP production. For example, co-cultivation of *L. plantarum* BAA-793 with *B. ovatus* +1194+PAD strain boosted 4EP level compared to *B. ovatus* +1194 strain without the PAD inserted cocolonized with *L. plantarum*.

FIG. 3B illustrates 4EP detection from in vitro coculture of engineered *B. ovatus* overexpressing BO1194 and PAD (chromosomal insertion of overexpressed BO1194, and PAD "Engineered BO" or "Eng. BO") or the BO1194 deletion mutant ("Mutant BO") with *L. plantarum*. As shown in FIG. 3B, the BO1194 deletion mutant *B. ovatus* in accordance with some embodiments herein failed to produce 4EP in co-culture. On the other hand the *B. ovatus* overexpressing BO1194 and PAD produced substantial quantities of 4EP in co-culture.

Figure 3C:
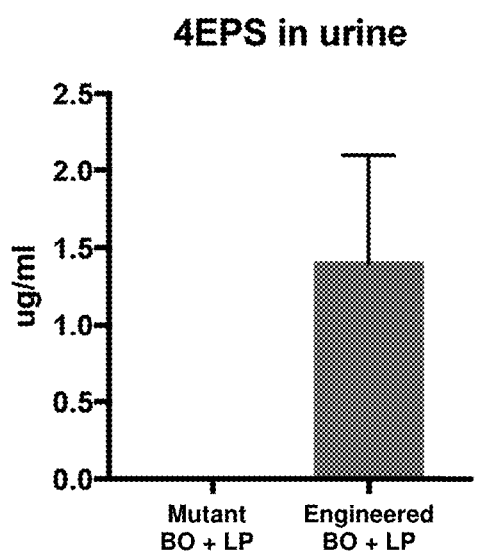

FIG. 3C illustrates quantitation of 4EPS in urine of ex-germ free mice cocolonized with BO and LP strain pairs (n=5). As shown in FIG. 3C, the mice co-colonized with the BO1194 deletion mutant did not have any detectable 4EPS in their urine. On the other hand, substantial quantities of 4EPS were detected in the urine of mice co-colonized with *B. ovatus* overexpressing BO1194.

These experiments show that colonizing the gut of a mammalian host with *B. ovatus* containing a loss-of-function mutation in BO1194 impairs the production of 4EPS in the mammal. These experiments further show that colonizing the gut of a mammalian host with *B. ovatus* overexpressing BO1194 yields higher expression of 4EPS.

Example 4: Anxiety Behavior of Mice Injected with 4EPS

Wildtype mice were injected intraperitoneally (i.p.) with saline or 30 mg/kg 4EPS potassium salt daily from 3 to 6 weeks of age and tested for anxiety in the elevated plus maze (FIG. 4A-C), light dark box (FIG. 4D-F), and open field arena (FIG. 4G-I) assays.

Figure 4A:
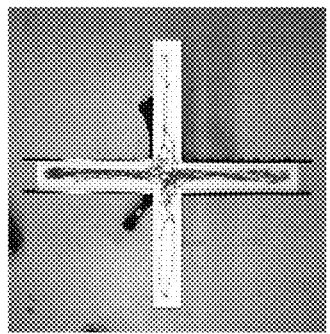
FIGS. 4A-I are a series of schematic images and graphs showing embodiments of responses to 4EPS injections.
Figure 4B:
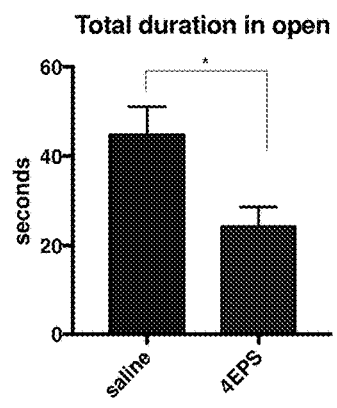
Figure 4C:
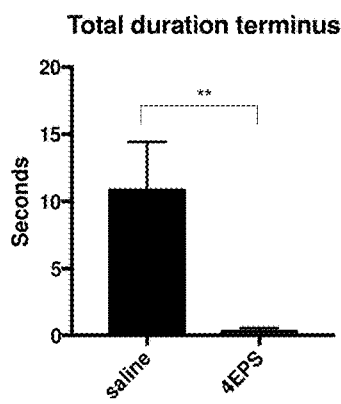
Figure 4D:
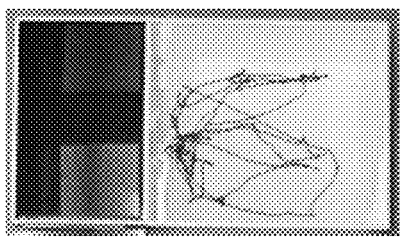
Figure 4E:
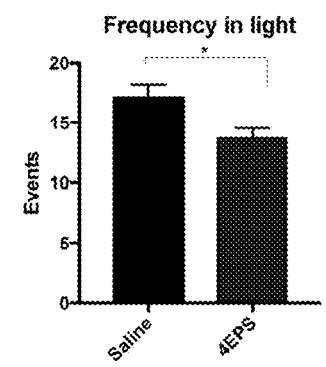
Figure 4F:
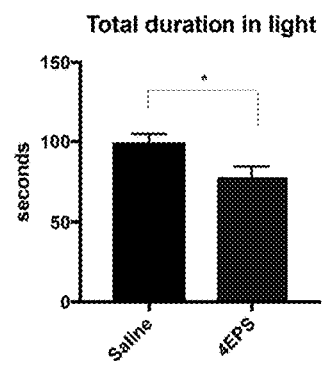
Figure 4G:
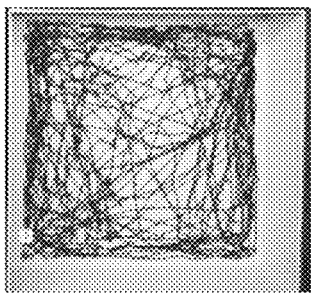
Figure 4H:
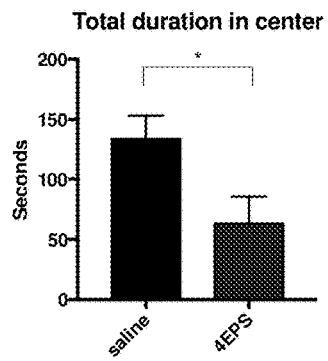
Figure 4I:
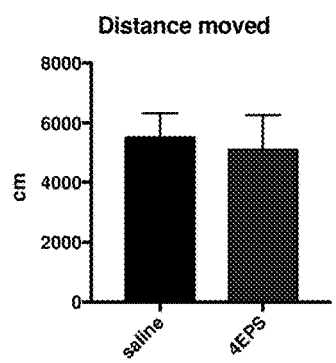

As shown in FIGS. 4A-4C, the mice injected with 4EPS exhibited decreased duration in the open, and decreased total terminus duration. As shown in FIGS. 4D-F, the mice injected with 4EPS exhibited decreased frequency and total duration in the light. As shown in FIGS. 4G-I, the mice injected with 4EPS exhibited decreased total duration in center. Distance moved was comparable to saline-injected mice.

These results indicate increasing the level of 4EPS in mice induces symptoms associated with anxiety.

Figure 5A:
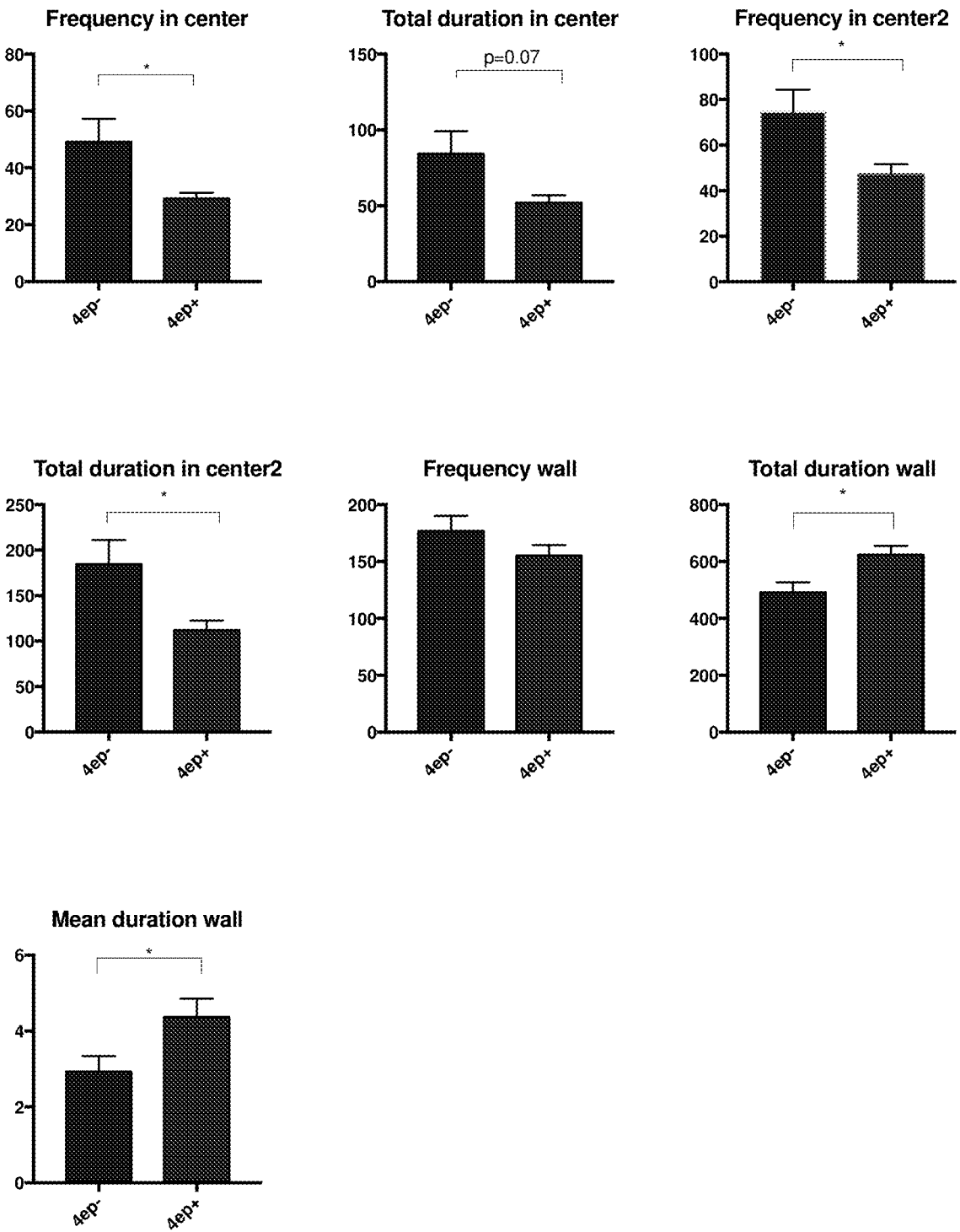
FIGS. 5A-B are a series of graphs showing open field arena behavior of mice colonized with 4EP+/− bacterial pairs of some embodiments herein.
Figure 5B:
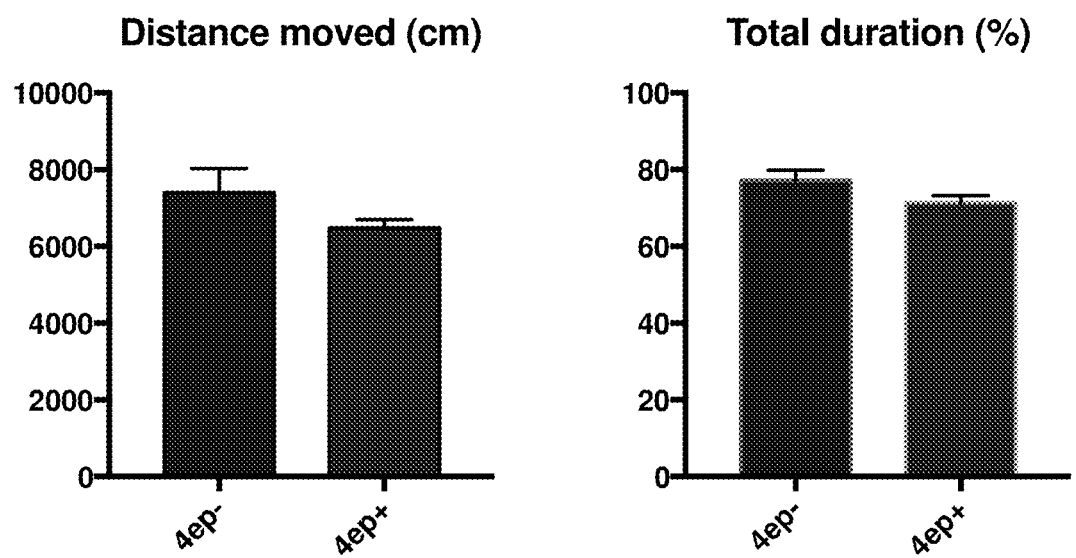

Example 5: Open Field Arena Behavior of Mice Colonized with 4EP+/− Bacterial Pairs Germ free mice were cocolonized by gavage of $10^8$ CFU of B. ovatus either with or without the 4EP biosynthetic pathway along with L. plantarum at 3 weeks of age (mutants were produced as described in Example 3). Mice were tested for anxiety-like (and ASD-like) behavior in the open field test at 7-8 weeks. Frequency of entries in to a segment of the arena as well as total duration of time spent there are shown in FIG. 5A. Total distance moved and total time spent moving are shown in FIG. 5B. Center=innermost section of arena. Center2=section between wall and center.

These data show that co-colonizing mice with B. ovatus containing a deletion mutation in BO1194 (and therefore deficient in producing 4EPS) in accordance with some embodiments herein ameliorated anxiety in mice (including, for example, anxiety associated with ASD) as measured in an open field arena, for example increasing frequency in center and total duration in center, and decreasing total duration at wall and mean duration at wall.

Figure 6B:
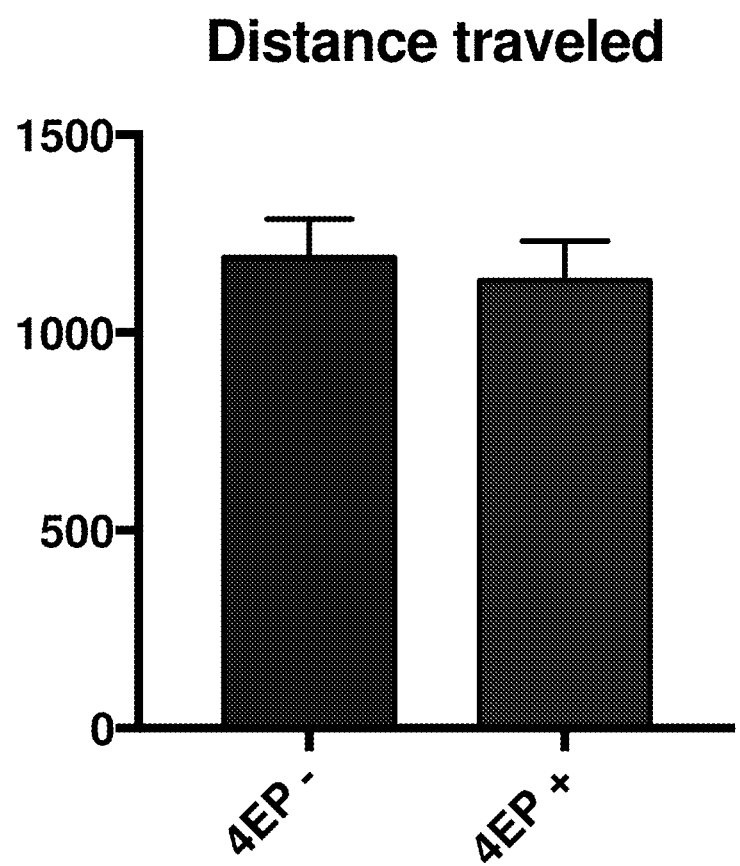

Example 6: Elevated Plus Maze (EPM) Behavior of Mice Colonized with 4EP+/− Bacterial Pairs Germ free mice were co-colonized by gavage of $10^8$ CFU of B. ovatus (+/− BO1194) and L. plantarum at 3 weeks of age and tested for anxiety-like and ASD-like behavior in the elevated plus maze test at 7-8 weeks. Frequency of entries in to a segment of the maze as well as total duration of time spent there is shown in FIG. 6A. Total distance moved is shown in FIG. 6B. Mid-outer=outer ⅔ of open arm. Terminus=outermost ⅓ of open arm. Closed=entire closed arm. Open=entire open arm.

These data show that co-colonizing mice with B. ovatus containing a deletion mutation in BO1194 (and therefore deficient in producing 4EPS) in accordance with some embodiments herein ameliorated anxiety in mice (including, for example, anxiety associated with ASD), as measured in an elevated plus maze, for example increasing total duration in center and total duration in center, and decreasing total duration at wall and mean duration at wall.

Figure 7A:
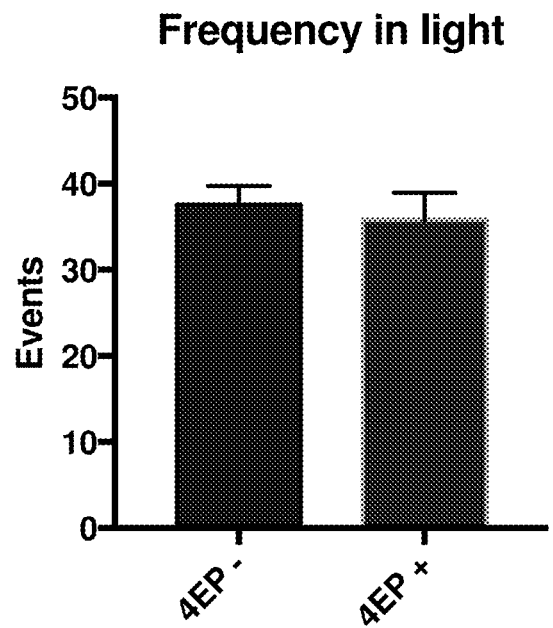
FIGS. 7A-C are a series of graphs showing light/dark box behavior of mice colonized with 4EP+/− bacterial pairs of some embodiments herein. Shown are frequency in light (FIG. 7A), total duration in light (FIG. 7B), and latency of first entry (FIG. 7C).
Figure 7B:
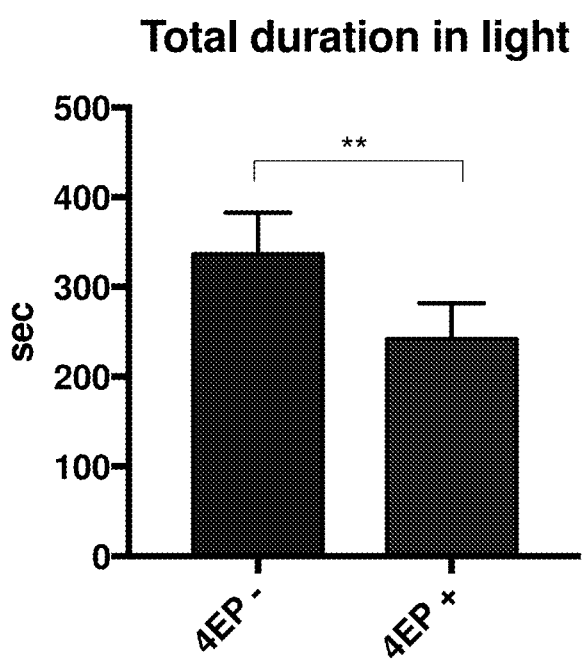
Figure 7C:
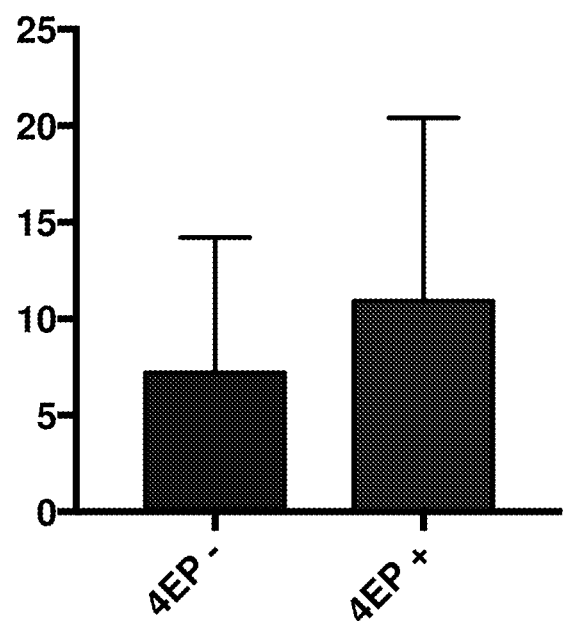

Example 7: Light/Dark Box Behavior of Mice Colonized with 4EP+/− Bacterial Pairs Germ free mice were cocolonized by gavage of $10^8$ CFU of B. ovatus (+/− BO1194) and L. plantarum at 3 weeks of age and tested for anxiety-like behavior in the light/dark box test at 7-8 weeks. Frequency of entries in to light chamber, total duration spent in light, and the latency of the first entry in to light chamber are shown in FIGS. 7A-C. Frequency in light were comparable for mice co-colonized with B. ovatus containing a deletion mutation in BO1194 (and therefore deficient in producing 4EPS) and for wild-type mice (FIG. 7A), and no statistically significant difference was observed for latency of first entry (FIG. 7C). On the other hand, the mice co-colonized with the mutant B. ovatus (and therefore deficient in producing 4EPS) exhibited significantly lower total duration in light (FIG. 7B).

These data show that co-colonizing mice with B. ovatus containing a deletion mutation in BO1194 (and therefore deficient in producing 4EPS) in accordance with some embodiments herein was effective in ameliorating symptoms associated with anxiety in mice (including, for example, anxiety associated with ASD), as measured by total duration in light in a light/dark box.

Example 8: Repetitive Behaviors of Mice Colonized with 4EP+/− Bacterial Pairs

Figure 8A:
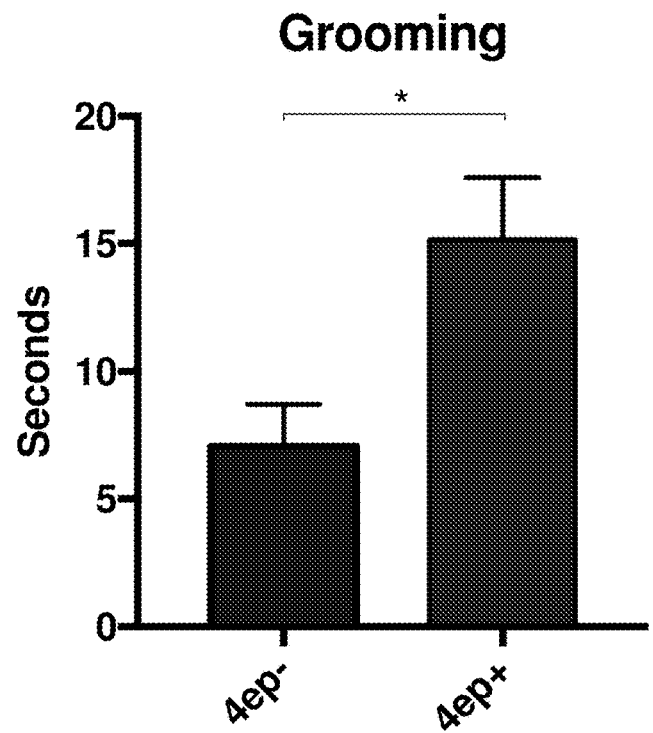
FIGS. 8A-C are a series of graphs showing repetitive behavior scores of mice colonized with engineered bacteria either lacking or producing 4EP of some embodiments herein. Shown are grooming behavior (FIG. 8A), digging behavior (FIG. 8B), and marble burying behavior (FIG. 8C).

Repetitive behavior scores were determined for mice colonized with engineered bacteria either lacking or producing 4EP. Mice were video recorded during a 10 minute period of social interaction with a novel mouse. Self-grooming was scored from manual video analysis, and the results are shown in FIG. 8A. The mice colonized with mutant bacteria deficient in 4EPS production exhibited significantly less grooming behavior (FIG. 8A).

Figure 8B:
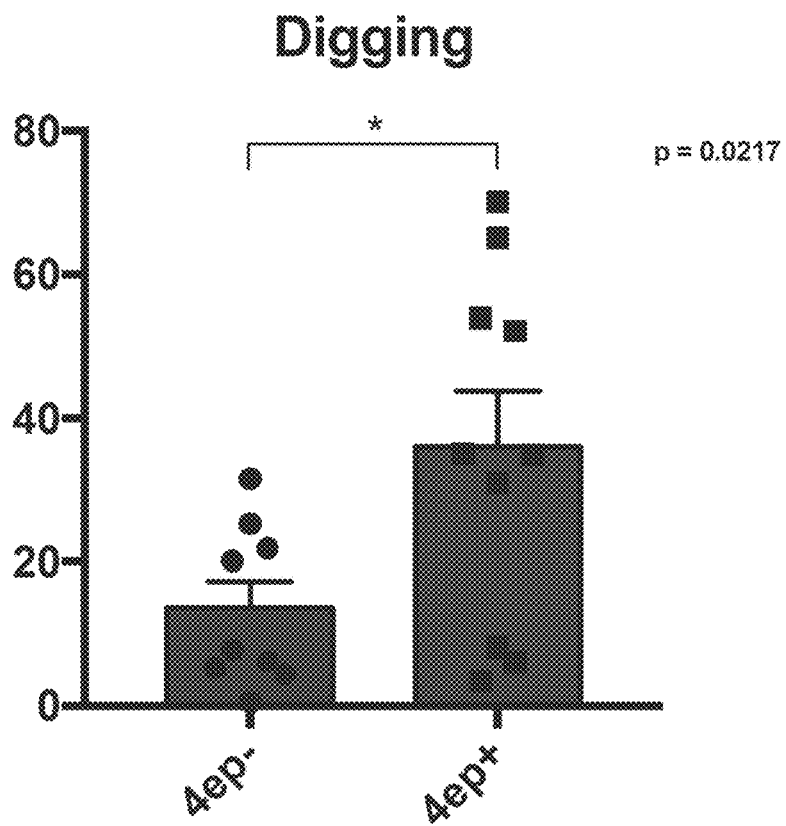

Mice were placed alone in a cage with a 1 inch layer of bedding and video recorded for 10 minutes. Digging behavior was scored from manual video analysis, and the results are shown in FIG. 8B. The mice colonized with mutant bacteria deficient in 4EPS production exhibited significantly less digging behavior (FIG. 8B).

Figure 8C:
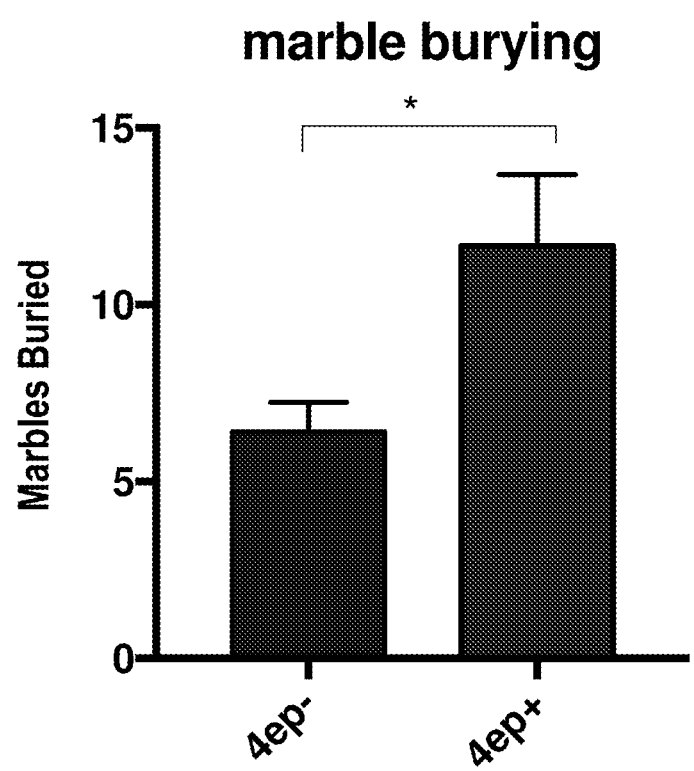

Mice were habituated to a new cage with 20 marbles laid in a grid pattern. Number of marbles buried after 10 minutes was scored, and the results are shown in FIG. 8C. The mice colonized with mutant bacteria deficient in EPS production exhibited significantly less marble burying behavior (FIG. 8C).

These data show that co-colonizing mice with B. ovatus containing a deletion mutation in BO1194 (and therefore deficient in producing 4EPS) in accordance with some embodiments herein ameliorated symptoms associated with anxiety and ASD in mice including repetitive behaviors, for example those measured by grooming, digging, and marble burying.

Example 9: Ultrasonic Vocalization Assay Behaviors of Mice Colonized with 4EP+/− Bacterial Pairs An ultrasonic vocalization assay was performed as an assay of communication behavior. Male mice colonized with engineered bacteria either lacking or producing 4EP were exposed to female mice for 15 minutes daily for 5 days. On the $6^{th}$ day, each individual mouse was introduced to a novel female and frequency and duration of ultrasonic vocalizations was recorded for 3 minutes. The results are shown in FIGS. 9A-B. Frequency (FIG. 9A) and duration (FIG. 9B) of the ultrasonic vocalization was significantly higher in the mice treated with B. ovatus containing a deletion mutation in BO1194 (and therefore deficient in producing 4EPS), compared to controls treated with 4EPS-producing bacteria.

These data show that co-colonizing mice with B. ovatus containing a deletion mutation in BO1194 (and therefore deficient in producing 4EPS) in accordance with some embodiments herein ameliorated a symptoms associated with anxiety and ASD in mice, including improving communication behaviors, as measured by ultrasonic vocalization.

Figure 10:
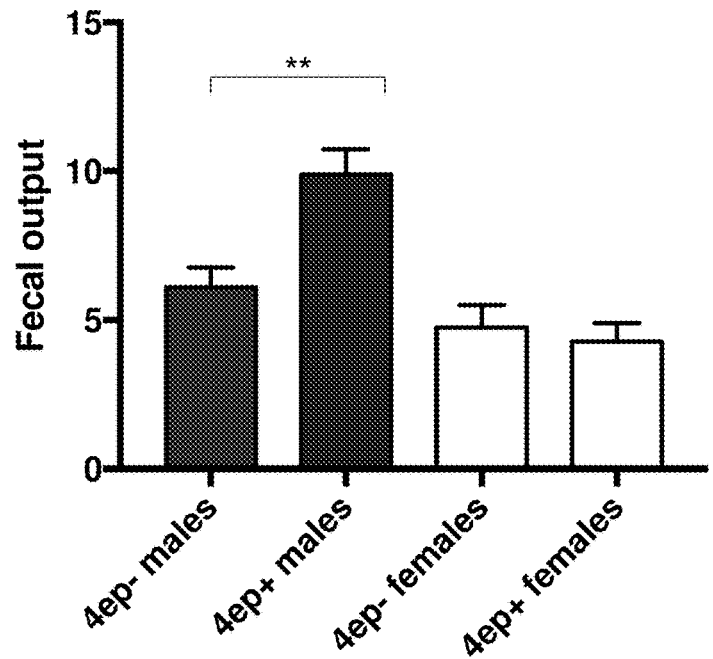
FIG. 10 is a graph showing fecal pellets produced in an open field assay for mice colonized with engineered bacteria either lacking or producing 4EP.

Example 10: Open Field Assay of Behaviors of Mice Colonized with 4EP+/− Bacterial Pairs During open field assay, fecal pellets of mice colonized with engineered bacteria either lacking or producing 4EP were counted. The 4EP-deficient ("4EP-") males had significantly lower fecal output than the wild-type control males (FIG. 10).

These data show that co-colonizing mice with *B. ovatus* containing a deletion mutation in BO1194 (and therefore deficient in producing 4EPS) in accordance with some embodiments herein lowered fecal output.

Example 11: Sulfation of 4EP and Modulation of the Same

Figure 11A:
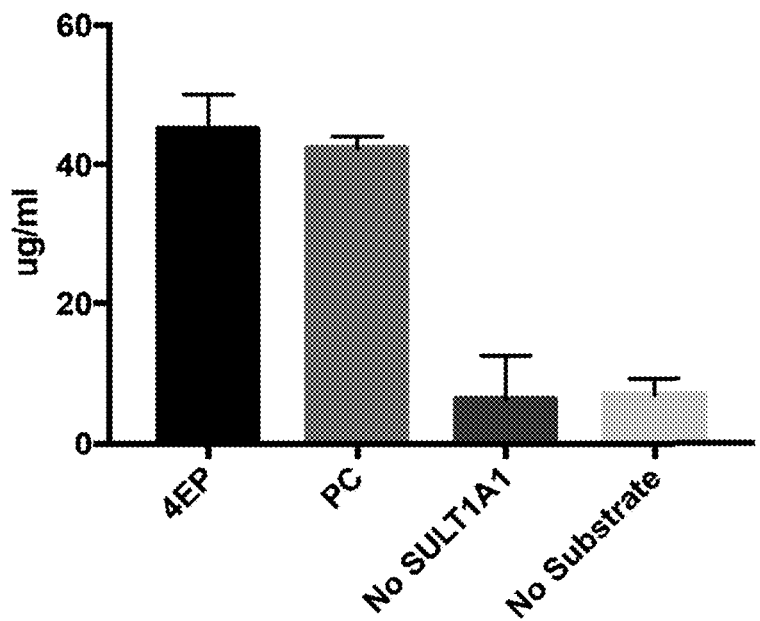
FIGS. 11A-E are a series of graphs illustrating analysis of sulfation of 4-ethylphenol (4EP) or para-cresol (PC) in accordance with some embodiments herein.
Figure 11B:
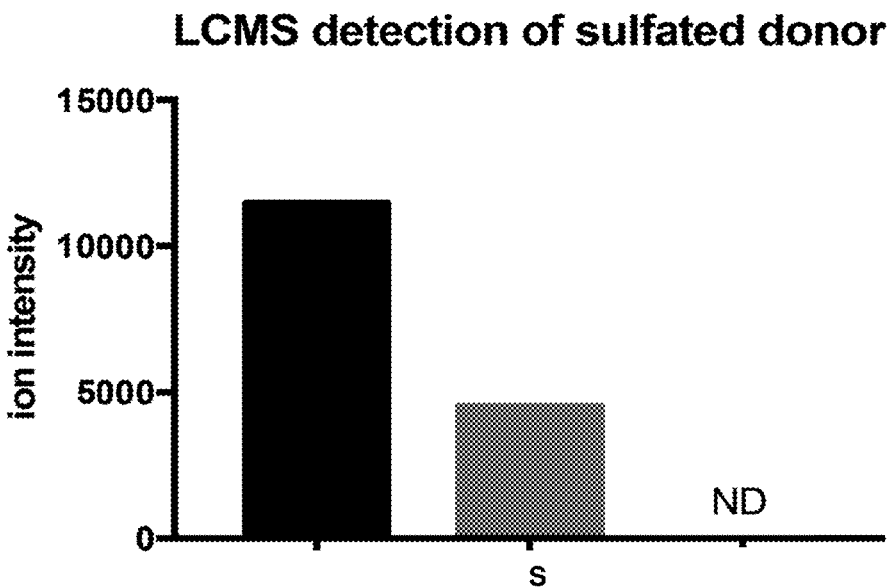

Using R&D SYSTEMS Universal Sulfotransferase Assay Kit™, sulfation of 4-ethylphenol (4EP) or para-cresol (PC) was determined colorimetrically (FIG. 11A). Samples from the assay were pooled and analyzed by liquid chromotography mass spectrometry (LCMS) for the confirmation that 4EPS and PCS are present (FIG. 11B). These experiments show that sulfated 4EP and PC can be detected in accordance with some embodiments herein.

Figure 11C:
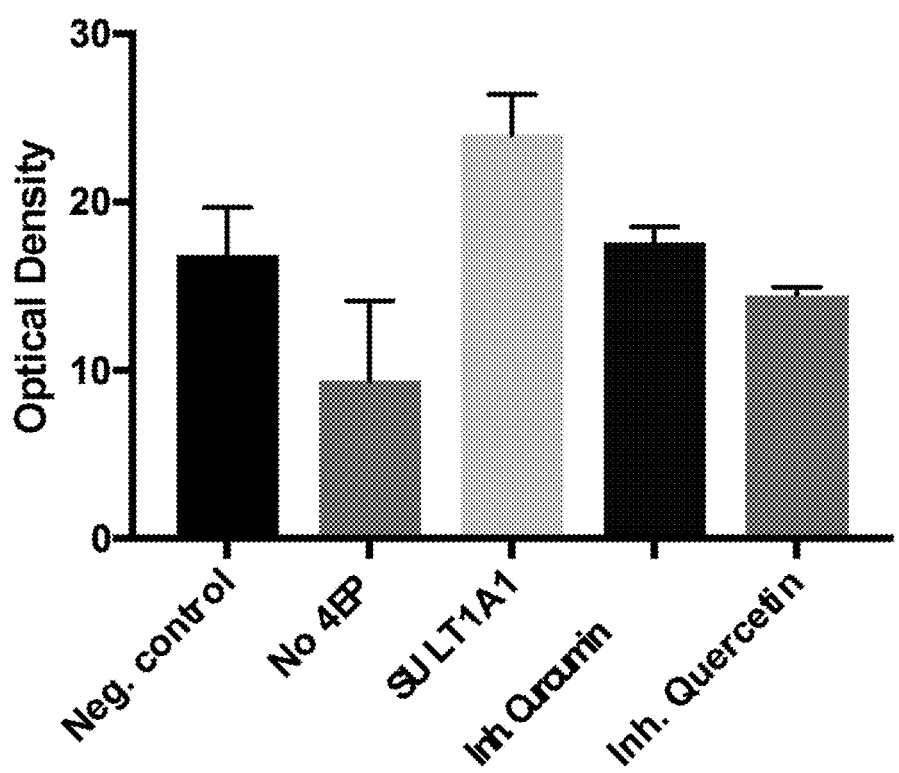

An R&D SYSTEMS assay was used to determine whether quercetin and curcumin can inhibit Sult1A1 (sulfotransferase family 1A member 1, an enzyme that catalyzes sulfate conjugation) modification of 4EP to 4EPS (FIG. 11C). These data show that quercetin and curcumin inhibit sulfation of 4EP in vitro. Accordingly, it is contemplated that quercetin and curcumin in accordance with some embodiments herein can inhibit the production of 4EPS in a subject in need thereof.

Figure 11D:
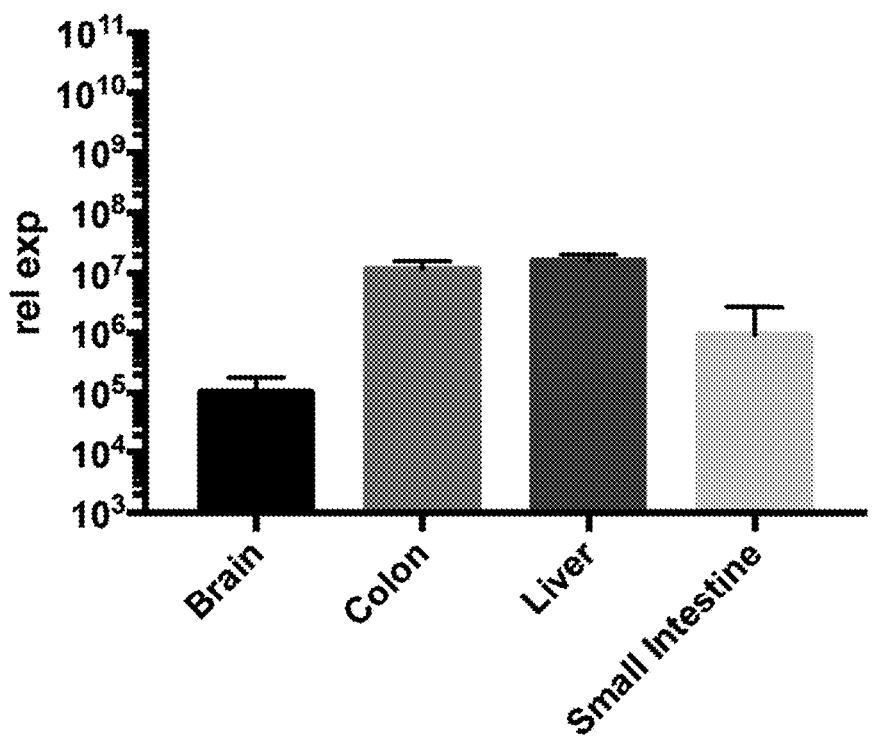

SULT1a1 gene expression was measured in various tissues of mice colonized with engineered bacteria deficient in producing 4EPS (FIG. 11D). It was observed that SULT1a1 is expressed in the GI tract of mice colonized with the bacteria.

Figure 11E:
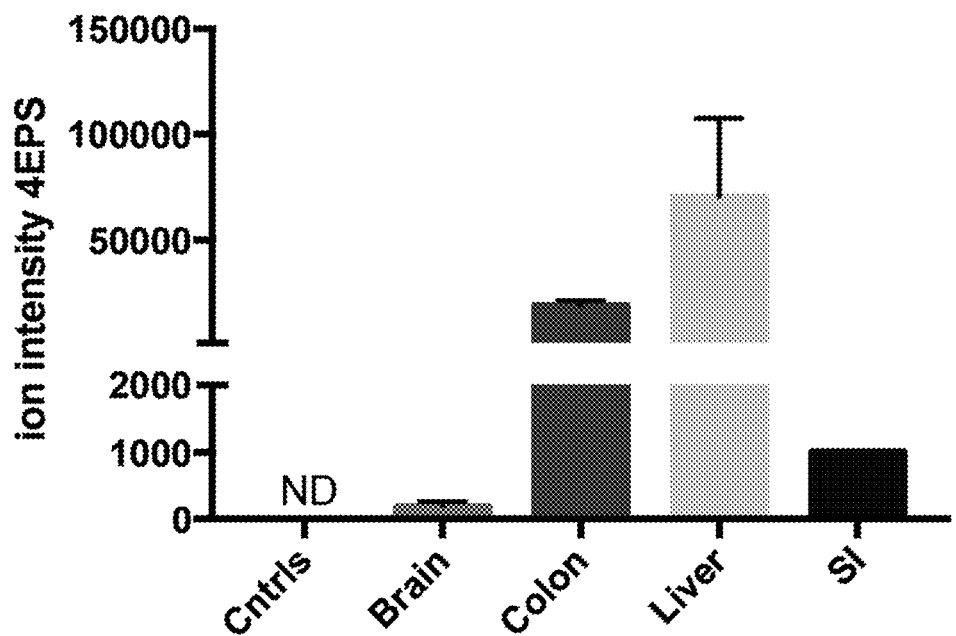

4EP to 4EPS conversion was measured by cytosolic fractions from various tissues of colonized mice (FIG. 11E). Substantial conversion of 4EP to 4EPS was observed in the colon and liver.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods, compositions, kits, and uses described herein without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one of skill in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Wherever a method of using a composition or product combination (e.g., a composition or product combination comprising, consisting essentially of, or consisting of a bacteria and/or an antibiotic) is disclosed herein, the corresponding composition for use is also expressly contemplated. For example, for the disclosure of a method of reducing or preventing a symptom of anxiety and/or ASD in a selected subject, comprising administering an amount of a composition comprising genetically modified *Bactericides ovatus*, and/or genetically modified *Lactobacillus plantarum*, and/or a polyphenol to the subject, the corresponding composition comprising *Bactericides ovatus* and/or *Lactobacillus plantarum*, and/or a polyphenol for use in reducing the likelihood of, delaying the onset of, or ameliorating one or more symptoms associated with anxiety and/or ASD is also contemplated.

While various aspects and embodiments have been disclosed herein, other aspects and embodiments will be apparent to those of skill in the art. The various aspects and embodiments disclosed herein are for purposes of illustration and are not intended to be limiting, with the true scope and spirit being indicated by the following claims.

What is claimed is:

1. A composition or product combination comprising a genetically engineered *Bacteroides ovatus* comprising a loss-of-function mutation in a gene encoding BO1194, and a genetically engineered *Lactobacillus plantarum* comprising a loss-of function mutation in a gene encoding phenolic acid decarboxylase (PAD).

2. The composition or product combination of claim 1, wherein the composition or product combination is formulated for oral or rectal administration to a mammalian subject.

3. The composition or product combination of claim 1, wherein the composition or product combination is selected from the group consisting of: a probiotic composition or product combination, a pharmaceutical composition or product combination, a dietary supplement, and a food; or a combination of two or more of the listed items.

4. A method of reducing or inhibiting production of 4-ethylphenol (4EP) and/or 4-ethylphenyl sulfate (4EPS) in a subject in need thereof, the method comprising:

a) administering to the subject a therapeutically effective amount of a composition or product combination comprising a genetically engineered *Bacteroides ovatus* comprising a lose-of-function mutation in a gene encoding BO 1194, and a genetically engineered *Lac-*

*tobacillus plantarum* comprising a loss-of-function mutation in a gene encoding phenolic acid decarboxylase (PAD); and b) permitting the genetically engineered *Bacteroides ovatus* and the genetically engineered *Lactobacillus plantarum* to proliferate in a gastrointestinal tract of the subject, whereby production of 4EP and/or 4EPS in the subject is reduced or inhibited.

5. The method of claim 4, wherein reducing the levels of 4EP and/or 4EPS ameliorates, delays the onset of, or decreases the likelihood of a symptom associated with anxiety and/or autism spectrum disorder (ASD) in the subject.

6. The method of claim 4, further comprising, prior to said administering, selecting the subject as being within a class of subjects that are in need of receiving the composition or product combination.

7. The method of claim 6, wherein said selecting comprises identifying the subject as having a symptom associated with anxiety and/or ASD.

8. The composition or product combination of claim 1, further comprising a polyphenol.

9. The composition or product combination of claim 8, wherein the polyphenol comprises quercetin or curcumin.

10. The composition or product combination of claim 1, wherein the loss-of-function mutation in the gene encoding BO1194 is a deletion, insertion, substitution, rearrangement, or frameshift.

11. The composition or product combination of claim 1, wherein the loss-of-function mutation in the gene encoding PAD is a deletion, insertion, substitution, rearrangement, or frameshift.

12. The composition or product combination of claim 1, wherein the genetically engineered *Bacteroides ovatus* is deficient in the production of p-coumaric acid.

13. The composition or product combination of claim 1, wherein the genetically engineered *Lactobacillus plantarum* is deficient in the production of 4-vinylphenol.

14. The composition or product combination of claim 1, wherein the composition or product combination comprises no more than $10^6$ cfu of *Lactobacillus plantarum*.

15. The composition or product combination of claim 1, wherein the composition or product combination comprises no more than $10^6$ cfu of *Bacteroides ovatus*.

16. The composition or product combination of claim 1, wherein the composition or product combination comprises at least $10^4$ cfu of the genetically engineered *Bacteroides ovatus*.

17. The composition or product combination of claim 1, wherein the composition or product combination comprises at least $10^4$ cfu of the genetically engineered *Lactobacillus plantarum*.

18. The composition or product combination of claim 1, further comprising *Bacteroides fragilis* or *Bacteroides thetaiotaomicron*.

19. The composition or product combination of claim 1, wherein the probiotic composition or product combination is present in a food product.

20. The composition or product combination of claim 1, further comprising a pharmaceutically acceptable carrier or excipient.

* * * * *

UNITED STATES PATENT AND TRADEMARK OFFICE
CERTIFICATE OF CORRECTION

PATENT NO. : 11,224,624 B2
APPLICATION NO. : 16/485403
DATED : January 18, 2022
INVENTOR(S) : Needham et al.

It is certified that error appears in the above-identified patent and that said Letters Patent is hereby corrected as shown below:

On the Title Page

Item (54) (Title), Line 2, delete "4-ETYLPHENOL" and insert -- 4-ETHYLPHENOL --.

In the Specification

Column 1, Line 2 (approx.), delete "4-ETYLPHENOL" and insert -- 4-ETHYLPHENOL --.

Column 3, Line 20, delete "thetaiotaomicro." and insert -- thetaiotaomicron. --.

Column 7, Line 18, delete "liklihoood" and insert -- likelihood --.

Column 10, Line 60, delete "curcumin)" and insert -- curcumin --.

Column 11, Line 44, delete "BO194," and insert -- BO1194, --.

Column 13, Line 20, delete "BO194" and insert -- BO1194 --.

Column 14, Line 20, delete "cfu" and insert -- cfu, --.

Column 16, Line 50, delete "(See." and insert -- (See, --.

Column 21, Line 17, delete "population" and insert -- population. --.

Column 21, Line 51, delete "(BCAOVA_1194" and insert -- (BACOVA_01194 --.

Column 22, Line 64, delete "(FIG." and insert -- (FIGS. --.

Column 22, Line 64, delete "(FIG." and insert -- (FIGS. --.

Signed and Sealed this
Tenth Day of May, 2022

Katherine Kelly Vidal
*Director of the United States Patent and Trademark Office*

Column 22, Line 65, delete "(FIG." and insert -- (FIGS. --.

Column 25, Line 15-16, delete "chromotography" and insert -- chromatography --.

In the Claims

Column 42, Line 67, Claim 4, delete "BO 1194," and insert -- BO1194, --.

SEQUENCE LISTING

<160> NUMBER OF SEQ ID NOS: 5

<210> SEQ ID NO 1
<211> LENGTH: 1524
<212> TYPE: DNA
<213> ORGANISM: Bacteroides ovatus

<400> SEQUENCE: 1

```
atgatagctg acaaaagtat aaatttagat acccttcata aagtattgtt tgataatgag      60
aagctgaaac tctctgaaga atgtattcga aaagtagaag aaagcttcga ttttctgcaa     120
tccttttcca gcgataagat tatttatggt atcaatacgg ggttcggccc aatggcacaa     180
tacagaatag aagatcagtc attgatcgac cttcagtata atatcatccg aagccattcc     240
accggtgccg gcaaaccgct tcccgaactt tatgtaaaag cagctatgat tgcccgtttg     300
tacacttttc tacaagggaa gtcaggagtg catctggaac tggtttctct cctctgtgaa     360
tttatcaacc gcggaattta tccgttcata cccgaacacg gaagtgtagg tgccagcggc     420
gatctcgtac aactggccca tatcgccctg acgttaatag gggaagggga agtttttat      480
cagggtaaat tgtgtaacgc agctacggta cttcaggaaa acggcctgaa accttttcc      540
atgcgtattc gtgaaggttt atccgttaca aacggtactt ctgtaatgac aggcatcggt     600
attgtcaatc tgatttatgc aaaaaaacta ctccgttggt cggtggctgc ctctgtaatg     660
atgaatgaga ttgccgcctc ttatgatgat tttatggcac aggcattaaa cgaggccaag     720
catcataaag gtcaacaaga gatagctgct atgatgagag aatgggtggc aggcagtaaa     780
tccgtgcttc aaagagagaa cgagctatac aaccaggtgc ataaagagaa aatcttcgaa     840
cacaaagtac agccctatta ttccttgcga tgtgttccgc aaatactcgg tcctatttac     900
gatgaactgg agaatgcgga agaagtatta ataaacgaaa taaattccgc ctgtgacaat     960
ccgattgtcg atccggatac acaaaatatt tatcatggcg gcaacttcca cggagattac    1020
atttctttcg aaatggacaa gttgaaaatt gctgtgacca agctgactat gctttgcgaa    1080
agacaaatta actatctgtt ccacgaccgt atcaatggca tcctgcctcc gtttgtaaat    1140
ttgggagtgc ttggattgaa ctatggttta caggcttcgc aattcactgc aacctccacc    1200
acagcggagt gtcagacatt atcaaatccg atgtatgtac acagtatccc caacaacaat    1260
gataatcagg atattgtcag catgggaacc aactcggctc tattagcaaa aacagtcatt    1320
gagaattctt atcaggtgat ggctatccag tttatgggaa tggcacaagc tatcgactac    1380
ctgaaaatac aggatcgcct aagttccaaa agcaggcagg tttatgaaga aatacgcagt    1440
ttcttccctg tatttaccaa tgacacacct aaatataaag agatagaaat gatgatagac    1500
tatctcaaaa aagaagataa ataa                                            1524
```

<210> SEQ ID NO 2
<211> LENGTH: 537
<212> TYPE: DNA

<213> ORGANISM: Lactobacillus plantarum

<400> SEQUENCE: 2

```
atgacaaaaa cttttaaaac acttgatgac tttctcggca cacactttat ctacacttat    60
gataacggct gggaatacga gtggtacgcc aagaacgacc acaccgttga ttaccgaatc   120
cacggtggga tggttgccgg tcgttgggtc actgatcaaa aagctgacat cgtcatgttg   180
accgaaggca tttacaaaat ttcttggact gaaccaactg ggactgacgt tgcactagac   240
ttcatgccca atgagaagaa actacacggt acgattttct tcccaaagtg ggttgaagaa   300
caccctgaaa ttacggtcac ttaccaaaac gaacacatcg atttaatgga acagtctcgt   360
gaaaagtatg ccacttatcc aaaactagtt gtacccgaat tgccaatat tacttacatg   420
ggcgacgccg gccaaaacaa cgaagatgta atcagtgaag caccttacaa agaaatgccg   480
aatgatattc gcaacggcaa gtactttgat caaaactacc atcgtttaaa taagtaa      537
```

<210> SEQ ID NO 3
<211> LENGTH: 7327
<212> TYPE: DNA
<213> ORGANISM: Artificial Sequence
<220> FEATURE:
<223> OTHER INFORMATION: pNBU2 with BCAOVA_1194 and PAD inserted in tandem

<400> SEQUENCE: 3

```
caattcgagg gggatcaatt ccgtgatagg tgggctgccc ttcctggttg gcttggtttc    60
atcagccatc cgcttgccct catctgttac gccggcggta gccggccagc ctcgcagagc   120
aggattcccg ttgagcaccg ccaggtgcga ataagggaca gtgaagaagg aacacccgct   180
cgcgggtggg cctacttcac ctatcctgcc cggctgacgc cgttggatac accaaggaaa   240
gtctacacga acccttggc aaaatcctgt atatcgtgcg aaaaggatg gatataccga    300
aaaaatcgct ataatgaccc cgaagcaggg ttatgcagcg gaaacggggg atccactagt   360
tctagaacgg aattgatccg gccacgatgc gtccggcgta gaggatctga agatcagcag   420
ttcaacctgt tgatagtacg tactaagctc tcatgtttca cgtactaagc tctcatgttt   480
aacgtactaa gctctcatgt ttaacgaact aaaccctcat ggctaacgta ctaagctctc   540
atggctaacg tactaagctc tcatgtttca cgtactaagc tctcatgttt gaacaataaa   600
attaatataa atcagcaact taaatagcct ctaaggtttt aagttttata agaaaaaaaa   660
gaatatataa ggcttttaaa gcttttaagg tttaacggtt gtggacaaca agccagggat   720
gtaacgcact gagaagccct tagagcctct caaagcaatt ttgagtgaca caggaacact   780
taacggctga catgggaatt ccctccacc gcggtggcgg ccgcgataaa acgaaaggct   840
cagtcgaaag actgggcctt tcgttttaca attgggctac cttttttttg ttttgtttgc   900
aatggttaat ctattgttaa aatttaaagt ttcacttgaa cttttcaaata atgttcttat   960
atttgcagtg tcgaaagaaa caaagtagat gatagctgac aaaagtataa atttagatac  1020
ccttcataaa gtattgtttg ataatgagaa gctgaaactc tctgaagaat gtattcgaaa  1080
agtagaagaa agcttcgatt ttctgcaatc cttttccagc gataagatta tttatggtat  1140
caatacgggg ttcggcccaa tggcacaata cagaatagaa gatcagtcat tgatcgacct  1200
tcagtataat atcatccgaa gccattccac cggtgccggc aaaccgcttc ccgaactta   1260
tgtaaaagca gctatgattg cccgtttgta cacttttcta caagggaagt caggagtgca  1320
tctggaactg gtttctctcc tctgtgaatt tatcaaccgc ggaatttatc cgttcatacc  1380
```

```
cgaacacgga agtgtaggtg ccagcggcga tctcgtacaa ctggcccata tcgccctgac    1440
gttaataggg gaaggggaag ttttttatca gggtaaattg tgtaacgcag ctacggtact    1500
tcaggaaaac ggcctgaaac cttttttccat gcgtattcgt gaaggtttat ccgttacaaa   1560
cggtacttct gtaatgacag gcatcggtat tgtcaatctg atttatgcaa aaaaactact    1620
ccgttggtcg gtggctgcct ctgtaatgat gaatgagatt gccgcctctt atgatgattt    1680
tatggcacag gcattaaacg aggccaagca tcataaaggt caacaagaga tagctgctat    1740
gatgagagaa tgggtggcag gcagtaaatc cgtgcttcaa agagagaacg agctatacaa    1800
ccaggtgcat aaagagaaaa tcttcgaaca caaagtacag ccctattatt ccttgcgatg    1860
tgttccgcaa atactcggtc ctatttacga tgaactggag aatgcggaag aagtattaat    1920
aaacgaaata aattccgcct gtgacaatcc gattgtcgat ccggatacac aaaatattta    1980
tcatggcggc aacttccacg gagattacat ttctttcgaa atggacaagt tgaaaattgc    2040
tgtgaccaag ctgactatgc tttgcgaaag acaaattaac tatctgttcc acgaccgtat    2100
caatggcatc ctgcctccgt tgtaaatttt gggagtgctt ggattgaact atggtttaca    2160
ggcttcgcaa ttcactgcaa cctccaccac agcggagtgt cagacattat caaatccgat    2220
gtatgtacac agtatcccca acaacaatga taatcaggat attgtcagca tgggaaccaa    2280
ctcggctcta ttagcaaaaa cagtcattga gaattcttat caggtgatgg ctatccagtt    2340
tatgggaatg cacaagcta tcgactacct gaaaatacag gatcgcctaa gttccaaaag    2400
caggcaggtt tatgaagaaa tacgcagttt cttccctgta tttaccaatg acacacctaa    2460
atataaagag atagaaatga tgatagacta tctcaaaaaa gaagataaat aagataaaac    2520
gaaaggctca gtcgaaagac tgggcctttc gttttacaat tgggctacct tttttttgtt    2580
ttgtttgcaa tggttaatct attgttaaaa tttaaagttt cacttgaact ttcaaataat    2640
gttcttatat ttgcagtgtc gaaagaaaca aagtagatga agtacagtaa aagactaagg    2700
agagtgtgta agatgaaaaa ctttatcgga agccacatga tttatacgta tgaaaacgga    2760
tgggaatacg agatttatat taaaaacgac catacaattg attatagaat tcatagcgga    2820
atggttgccg gacgctgggt tcgagatcag gaagtgaata ttgtcaaact gacagaaggc    2880
gtatataaag tgtcttggac agagccgact ggcacggatg tttcattaaa ctttatgcca    2940
aatgaaaaac gcatgcatgg cattattttc ttcccgaaat gggtgcatga acatcctgaa    3000
attacggttt gctaccaaaa tgaccacatt gatttgatga agaatcccg cgaaaaatat    3060 gaaacgtatc caaaatacgt tgtacctgaa tttgcggaaa ttacatttct gaaaaatgaa    3120
ggagtcgaca acgaagaagt gatttcgaag gctccttatg agggaatgac agacgatatt    3180
cgcgcgggaa gattataatc tagaactagt ggatccccg tctagaacta gtggatcccc    3240
cgggctgcag gaattcgata tcaagcttat cgataccgtc gactaattgc ctatcttcca    3300
gtgatggaac agcatttgtg cattggctgc aacaatcagc cttacttgtg cctgttctat    3360
ttccgaaccg accgcttgta tgaatccatc aaaattcgtt ttctctatgt tggattcctt    3420
gttgctcata ttgtgatgat aatttctaca aatatagtca ttggtaacta tctatgaaac    3480
tgtttgatac ttttatagtt gattaaactt gttcatggca tttgccttaa tatcatccgc    3540
tatgtcaatg tagggtttca tagctttgta gtcgctgtgt cccgtccatt tcatgaccac    3600
ctgtgccggg attccgagag ccagcgcatt gcagatgaat gtccttcttc ctgcatgggt    3660
actgagcaaa gcgtatttgg gtgtgacttc atcaatacgt tcatttccct tgtagtaggt    3720
ttcccgtaca ggctcgttga tttctgccag ttcgcccagc tctttcaggt aatcgttcat    3780
```

-continued

```
cttctggttg ctgatgacgg gcagagccat gtaattctcg aaatggatgt ccttgtattt    3840
gtccagtatg gctttgctgt atttgttcag ttcaatcgtc aggctgtcgg cagtcttgac    3900
tgtggttatt tcgatgtggt cggacttcac atcgcttctt ttcagattgc gaacatccga    3960
ataccgcaaa ctcgtaaagc agcagaacag gaaaacatca cgcacacgtt ccaggtattg    4020
cttatccttg ggtatctggt agtctttcag cttgttcagt tcatcccaag tcaggaagat    4080
tacttttttc gaggtggttt tcagtttcgg tttgaacgta tcgtatgcaa tgttctgatg    4140
atgtcctttc ttgaagctcc agcgcaggaa ccatttgagg aatcccattt gcttgccgat    4200
ggtgctgttt ctcatatcct tggtgtcacg caggaagttg acgtattcgt tcaatccaaa    4260
ctcgttgaaa tagttgaacg ttgcatcctc cttgaactct tgaggtggt tcctcactgc    4320 tgcaaatttt tcataggtgg atgccgtcca gttattctgg ttaccgcact cttttacaaa    4380
ctcatcgaac acctcccaaa agctgacagg ggcttcttcc ggctgttctt cgctggtgtc    4440
tttcattctc atgttgaaag cttccttcaa ctgttgggtc gttggcatga cctcctgcac    4500
ctcaaattcc ttgaaaatat tctggatttc ggcatagtat ttcagcaagt ccgtattgat    4560
ttcggctgca cttttgcttta gcttgttggt acatccgctc tttacccgct gcttatctgc    4620
atcccatttg gctacgtcaa tccggtagcc cgttgtaaac tcgatgcgtt ggctggcaaa    4680
gatgacacgc atacgatgg gtacgttctc tacgattggc acaccgttct tttccggct     4740 ctccaatgca aaaatgatgt tgcgcttgat attcataatt gggtgcgttt gaaattctac    4800
acccaaatat acacccaatt attgagatag caaaagacat ttagaaacat ttactttac    4860 tctatattgt aatttacact tgattatcag tcgtttgcag tcttatgata ttctgtgaaa    4920
gtataagttc gagagcctgt ctctccgcaa aaacgctga aaatcagcag attgcaaaac    4980
aaacaccctg ttttacaccc aagaatgtaa agtcggctgt ttttgtttta tttaagataa    5040
tacaaccact acataataaa agagtagcga tattaaaaga atccgatgag aaaagactaa    5100
tatttatcta tccattcagt ttgattttc aggactttac atcgtcctga aagtatttgt     5160
tggtaccggt accgaggacg cgtaaacatt tacagttgca tgtggcctat tgttttagc    5220 cgttaaatat tttataacta ttaaatagcg atacaaattg ttcgaaacta atattgttta    5280
tatcatatat tctcgcatgt tttaaagctt tattaaattg atttttgta aacagttttt     5340 cgtactcttt gttaacccat ttcattacaa agtttcata tttttttctc tctttaaatg    5400
ccatttttgc tggctttctt tttaatacaa ttaatgtgct atccacttta ggttttggat    5460
ggaaataata cctaggaatt tttgctaata tagaaatatc tacctctgcc attaacagca    5520
atgctagtga tctgtttgta tctaataaca ttttagcaaa accatattcc actattaaat    5580
aacttattgt ggctgaactt tcaaaaacaa ttttcgaat tatatttgtg cttatgttgt     5640
aaggtatgct gccaaatatt ttatatggat tgtggctagg aaatgtaaat ttcagtatat    5700 catcattac tatttgatag ttaggataat ttaagagctt attacgagtt acctcacata    5760
atttagaatc aatttctatc gccgttacaa aattacatct ctttaccaat ccagcagtaa    5820
aatgaccttt ccctgcacct atttcaaaga tgttatcttt ttcatctaaa cttatgcaat    5880
tcattatttt ttctatgtga tatttgaag taataaaatt ttgactatct tttatattta    5940
ctttgttcat tataacctct ccttaattta ttgcatctct tttcgaatat ttatgttttt    6000
tgagaaaaga acgtactcat ggttcatccc gatatgcgta tcggtctgta tatcagcaac    6060
tttctatgtg tttcaactac aatagtcatc tattctcatc tttctgagtc caccccctgc    6120
```

```
aaagcccctc tttacgacat aaaaattcgg tcggaaaagg tatgcaaaag atgtttctct    6180
ctttaagaga aactcttcgg gatgcaaaaa tatgaaaata actccaattc accaaattat    6240
atagcgactt ttttacaaaa tgctaaaatt tgttgatttc cgtcaagcaa ttgttgagca    6300
aaaatgtctt ttacgataaa atgataccct aatatcaact gtttagcaaa acgatatttc    6360
tcttaaagag agaaacacct ttttgttcac caatccccga ctttttaatcc cgcggccatg    6420 attgaaaaag gaagagtatg agtattcaac atttccgtgt cgcccttatt ccctttttttg    6480 cggcattttg ccttcctgtt tttgctcacc cagaaacgct ggtgaaagta aaagatgctg    6540
aagatcagtt gggtgcacga gtgggttaca tcgaactgga tctcaacagc ggtaagatcc    6600
ttgagagttt tcgccccgaa gaacgttttc caatgatgag cacttttaaa gttctgctat    6660
gtggcgcggt attatcccgt attgacgccg ggcaagagca actcggtcgc cgcatacact    6720
attctcagaa tgacttggtt gagtactcac cagtcacaga aaagcatctt acggatggca    6780
tgacagtaag agaattatgc agtgctgcca taaccatgag tgataacact gcggccaact    6840
tacttctgac aacgatcgga ggaccgaagg agctaaccgc ttttttgcac aacatggggg    6900
atcatgtaac tcgccttgat cgttgggaac cggagctgaa tgaagccata ccaaacgacg    6960
agcgtgacac cacgatgcct gtagcaatgg caacaacgtt gcgcaaacta ttaactggcg    7020
aactacttac tctagcttcc cggcaacaat taatagactg gatggaggcg gataaagttg    7080
caggaccact tctgcgctcg gcccttccgg ctggctggtt tattgctgat aaatctggag    7140
ccggtgagcg tgggtctcgc ggtatcattg cagcactggg gccagatggt aagccctccc    7200
gtatcgtagt tatctacacg acggggagtc aggcaactat ggatgaacga aatagacaga    7260
tcgctgagat aggtgcctca ctgattaagc attggtaact gtcagaccaa gtttactcat    7320
aacgcgt                                                              7327
```

<210> SEQ ID NO 4
<211> LENGTH: 6619
<212> TYPE: DNA
<213> ORGANISM: Artificial Sequence
<220> FEATURE:
<223> OTHER INFORMATION: pNBU2_phagep_B01

<400> SEQUENCE: 4

```
caattcgagg gggatcaatt ccgtgatagg tgggctgccc ttcctggttg gcttggtttc      60
atcagccatc cgcttgccct catctgttac gccggcggta gccgccagc ctcgcagagc     120 aggattcccg ttgagcaccg ccaggtgcga ataagggaca gtgaagaagg aacacccgct     180
cgcgggtggg cctacttcac ctatcctgcc cggctgacgc cgttggatac accaaggaaa     240
gtctacacga acccttttggc aaaatcctgt atatcgtgcg aaaaaggatg gatataccga     300
aaaaatcgct ataatgaccc cgaagcaggg ttatgcagcg gaaacggggg atccactagt     360
tctagaacgg aattgatccg gccacgatgc gtccggcgta gaggatctga agatcagcag     420
ttcaacctgt tgatagtacg tactaagctc tcatgtttca cgtactaagc tctcatgttt     480
aacgtactaa gctctcatgt ttaacgaact aaaccctcat ggctaacgta ctaagctctc     540
atggctaacg tactaagctc tcatgtttca cgtactaagc tctcatgttt gaacaataaa     600
attaatataa atcagcaact aaatagcct ctaaggtttt aagttttata agaaaaaaaa     660
gaatatataa ggcttttaaa gcttttaagg tttaacggtt gtggacaaca agccagggat     720
gtaacgcact gagaagccct tagagcctct caaagcaatt ttgagtgaca caggaacact     780
taacggctga catgggaatt cccctccacc gcggtggcgg ccgcgataaa acgaaaggct     840
```

```
cagtcgaaag actgggcctt tcgttttaca attgggctac cttttttttg ttttgtttgc    900
aatggttaat ctattgttaa aatttaaagt ttcacttgaa ctttcaaata atgttcttat    960
atttgcagtg tcgaaagaaa caaagtagat gatagctgac aaaagtataa atttagatac   1020
ccttcataaa gtattgtttg ataatgagaa gctgaaactc tctgaagaat gtattcgaaa   1080
agtagaagaa agcttcgatt ttctgcaatc cttttccagc gataagatta tttatggtat   1140
caatacgggg ttcggcccaa tggcacaata cagaatagaa gatcagtcat tgatcgacct   1200
tcagtataat atcatccgaa gccattccac cggtgccggc aaaccgcttc ccgaacttta   1260
tgtaaaagca gctatgattg cccgtttgta cacttttcta caagggaagt caggagtgca   1320
tctggaactg gtttctctcc tctgtgaatt tatcaaccgc ggaatttatc cgttcatacc   1380
cgaacacgga agtgtaggtg ccagcggcga tctcgtacaa ctggcccata tcgccctgac   1440
gttaataggg gaaggggaag ttttttatca gggtaaattg tgtaacgcag ctacggtact   1500
tcaggaaaac ggcctgaaac cttttttccat gcgtattcgt gaaggtttat ccgttacaaa   1560
cggtacttct gtaatgacag gcatcggtat tgtcaatctg atttatgcaa aaaaactact   1620
ccgttggtcg gtggctgcct ctgtaatgat gaatgagatt gccgcctctt atgatgattt   1680
tatggcacag gcattaaacg aggccaagca tcataaaggt caacaagaga tagctgctat   1740
gatgagagaa tgggtggcag gcagtaaatc cgtgcttcaa agagagaacg agctatacaa   1800
ccaggtgcat aaagagaaaa tcttcgaaca caaagtacag ccctattatt ccttgcgatg   1860
tgttccgcaa atactcggtc ctatttacga tgaactggag aatgcggaag aagtattaat   1920
aaacgaaata aattccgcct gtgacaatcc gattgtcgat ccggatacac aaaatattta   1980
tcatggcggc aacttccacg gagattacat ttctttcgaa atggacaagt tgaaaattgc   2040
tgtgaccaag ctgactatgc tttgcgaaag acaaattaac tatctgttcc acgaccgtat   2100
caatggcatc ctgcctccgt tgtaaaattt gggagtgctt ggattgaact atggtttaca   2160
ggcttcgcaa ttcactgcaa cctccaccac agcggagtgt cagacattat caaatccgat   2220
gtatgtacac agtatcccca acaacaatga taatcaggat attgtcagca tgggaaccaa   2280
ctcggctcta ttagcaaaaa cagtcattga gaattcttat caggtgatgg ctatccagtt   2340
tatgggaatg gcacaagcta tcgactacct gaaaatacag gatcgcctaa gttccaaaag   2400
caggcaggtt tatgaagaaa tacgcagttt cttccctgta tttaccaatg acacacctaa   2460
atataaagag atagaaatga tgatagacta tctcaaaaaa gaagataaat aatctagaac   2520
tagtggatcc cccgggctgc aggaattcga tatcaagctt atcgataccg tcgactaatt   2580
gcctatcttc cagtgatgga acagcatttg tgcattggct gcaacaatca gccttacttg   2640
tgcctgttct atttccgaac cgaccgcttg tatgaatcca tcaaaattcg ttttctctat   2700
gttggattcc ttgttgctca tattgtgatg ataatttcta caaatatagt cattggtaac   2760
tatctatgaa actgtttgat acttttatag ttgattaaac ttgttcatgg catttgcctt   2820
aatatcatcc gctatgtcaa tgtagggttt catagctttg tagtcgctgt gtcccgtcca   2880
tttcatgacc acctgtgccg ggattccgag agccagcgca ttgcagatga atgtccttct   2940
tcctgcatgg gtactgagca aagcgtattt gggtgtgact tcatcaatac gttcatttcc   3000
cttgtagtag gtttcccgta caggctcgtt gatttctgcc agttcgccca gctctttcag   3060
gtaatcgttc atcttctggt tgctgatgac gggcagagcc atgtaattct cgaaatggat   3120
gtccttgtat ttgtccagta tggctttgct gtatttgttc agttcaatcg tcaggctgtc   3180
```

```
ggcagtcttg actgtggtta tttcgatgtg gtcggacttc acatcgcttc ttttcagatt    3240
gcgaacatcc gaataccgca aactcgtaaa gcagcagaac aggaaaacat cacgcacacg    3300
ttccaggtat tgcttatcct tgggtatctg gtagtctttc agcttgttca gttcatccca    3360
agtcaggaag attactttt tcgaggtggt tttcagtttc ggtttgaacg tatcgtatgc     3420
aatgttctga tgatgtcctt tcttgaagct ccagcgcagg aaccatttga ggaatcccat    3480
ttgcttgccg atggtgctgt ttctcatatc cttggtgtca cgcaggaagt tgacgtattc    3540
gttcaatcca aactcgttga aatagttgaa cgttgcatcc tccttgaact ctttgaggtg    3600
gttcctcact gctgcaaatt tttcataggt ggatgccgtc cagttattct ggttaccgca    3660
ctcttttaca aactcatcga acacctccca aaagctgaca ggggcttctt ccggctgttc    3720
ttcgctggtg tctttcattc tcatgttgaa agcttcctc aactgttggg tcgttggcat     3780
gacctcctgc acctcaaatt ccttgaaaat attctggatt tcggcatagt atttcagcaa    3840
gtccgtattg atttcggctg cactttgctt tagcttgttg gtacatccgc tctttacccg    3900
ctgcttatct gcatcccatt tggctacgtc aatccggtag cccgttgtaa actcgatgcg    3960
ttggctggca aagatgacac gcatacggat gggtacgttc tctacgattg gcacaccgtt    4020
ctttttccgg ctctccaatg caaaaatgat gttgcgcttg atattcataa ttgggtgcgt    4080
ttgaaattct acacccaaat atacacccaa ttattgagat agcaaagac atttagaaac     4140
atttactttt actctatatt gtaatttaca cttgattatc agtcgtttgc agtcttatga    4200
tattctgtga agtataagt tcgagagcct gtctctccgc aaaaaacgct gaaaatcagc     4260
agattgcaaa acaaacaccc tgttttacac ccaagaatgt aaagtcggct gttttgttt     4320
tatttaagat aatacaacca ctacataata aagagtagc gatattaaaa gaatccgatg     4380
agaaaagact aatatttatc tatccattca gtttgatttt tcaggacttt acatcgtcct    4440
gaaagtattt gttggtaccg gtaccgagga cgcgtaaaca tttacagttg catgtggcct    4500
attgttttta gccgttaaat attttataac tattaaatag cgatacaaat tgttcgaaac    4560
taatattgtt tatatcatat attctcgcat gttttaaagc tttattaaat tgattttttg    4620
taaacagttt ttcgtactct tgttaaccc atttcattac aaaagtttca tatttttttc     4680
tctctttaaa tgccatttt gctggctttc ttttaatac aattaatgtg ctatccactt      4740
taggttttgg atggaaataa taccaggaa ttttgctaa tatagaaata tctacctctg      4800
ccattaacag caatgctagt gatctgtttg tatctaataa catttagca aaaccatatt     4860
ccactattaa ataacttatt gtggctgaac tttcaaaaac aattttcga attatatttg     4920
tgcttatgtt gtaaggtatg ctgccaaata ttttatatgg attgtggcta ggaaatgtaa    4980
atttcagtat atcatcattt actatttgat agtaggata atttaagagc ttattacgag     5040
ttacctcaca taatttagaa tcaatttcta tcgccgttac aaaattacat ctctttacca    5100
atccagcagt aaaatgacct ttccctgcac ctatttcaaa gatgttatct ttttcatcta    5160
aacttatgca attcattatt ttttctatgt gatatttga agtaataaaa ttttgactat     5220
cttttatatt tactttgttc attataacct ctccttaatt tattgcatct cttttcgaat    5280
atttatgttt tttgagaaaa gaacgtactc atggttcatc ccgatatgcg tatcggtctg    5340
tatatcagca actttctatg tgtttcaact acaaatagtca tctattctca tctttctgag    5400
tccacccct gcaagcccc tcttacgac ataaaaattc ggtcggaaaa ggtatgcaaa       5460
agatgttct ctcttaaga gaaactcttc gggatgcaaa aatatgaaaa taactccaat      5520
tcaccaaatt atatagcgac ttttttacaa aatgctaaaa tttgttgatt tccgtcaagc    5580
```

```
aattgttgag caaaaatgtc ttttacgata aaatgatacc tcaatatcaa ctgtttagca    5640
aaacgatatt tctcttaaag agagaaacac cttttgttc accaatcccc gacttttaat    5700
cccgcggcca tgattgaaaa aggaagagta tgagtattca acatttccgt gtcgccctta    5760 ttccctttt tgcggcattt tgccttcctg tttttgctca cccagaaacg ctggtgaaag    5820
taaaagatgc tgaagatcag ttgggtgcac gagtgggtta catcgaactg gatctcaaca    5880
gcggtaagat ccttgagagt tttcgccccg aagaacgttt tccaatgatg agcactttta    5940
aagttctgct atgtggcgcg gtattatccc gtattgacgc cgggcaagag caactcggtc    6000
gccgcataca ctattctcag aatgacttgg ttgagtactc accagtcaca gaaaagcatc    6060
ttacggatgg catgacagta agagaattat gcagtgctgc cataaccatg agtgataaca    6120
ctgcggccaa cttacttctg acaacgatcg gaggaccgaa ggagctaacc gcttttttgc    6180
acaacatggg ggatcatgta actcgccttg atcgttggga accggagctg aatgaagcca    6240
taccaaacga cgagcgtgac accacgatgc ctgtagcaat ggcaacaacg ttgcgcaaac    6300
tattaactgg cgaactactt actctagctt cccggcaaca attaatagac tggatggagg    6360
cggataaagt tgcaggacca cttctgcgct cggcccttcc ggctggctgg tttattgctg    6420
ataaatctgg agccggtgag cgtgggtctc gcggtatcat tgcagcactg gggccagatg    6480
gtaagccctc ccgtatcgta gttatctaca cgacggggag tcaggcaact atggatgaac    6540
gaaatagaca gatcgctgag ataggtgcct cactgattaa gcattggtaa ctgtcagacc    6600
aagtttactc ataacgcgt                                                  6619

<210> SEQ ID NO 5
<211> LENGTH: 522
<212> TYPE: DNA
<213> ORGANISM: Bacillus subtilis

<400> SEQUENCE: 5
atgaagtaca gtaaaagact aaggagagtg tgtaagatgg aaaactttat cggaagccac      60
atgatttata cgtatgaaaa cggatgggaa tacgagattt atattaaaaa cgaccataca     120
attgattata gaattcatag cggaatggtt gccggacgct gggttcgaga tcaggaagtg     180
aatattgtca aactgacaga aggcgtatat aaagtgtctt ggacagagcc gactggcacg     240
gatgtttcat taaactttat gccaaatgaa aaacgcatgc atggcattat tttcttcccg     300
aaatgggtgc atgaacatcc tgaaattacg gtttgctacc aaaatgacca cattgatttg     360
atgaaagaat cccgcgaaaa atatgaaacg tatccaaaat acgttgtacc tgaatttgcg     420
gaaattacat ttctgaaaaa tgaaggagtc gacaacgaag aagtgatttc gaaggctcct     480
tatgagggaa tgacagacga tattcgcgcg ggaagattat aa                       522
```